United States Patent
Ouchi

(10) Patent No.: US 12,415,777 B2
(45) Date of Patent: *Sep. 16, 2025

(54) FLUORENE DERIVATIVE, AND PRODUCTION METHOD AND USE FOR SAME

(71) Applicant: Osaka Gas Chemicals Co., Ltd., Osaka (JP)

(72) Inventor: Yuki Ouchi, Osaka (JP)

(73) Assignee: OSAKA GAS CHEMICALS CO., LTD., Osaka (JP)

(*) Notice: Subject to any disclaimer, the term of this patent is extended or adjusted under 35 U.S.C. 154(b) by 589 days.

This patent is subject to a terminal disclaimer.

(21) Appl. No.: 17/800,989

(22) PCT Filed: Feb. 24, 2021

(86) PCT No.: PCT/JP2021/006717
§ 371 (c)(1),
(2) Date: Aug. 19, 2022

(87) PCT Pub. No.: WO2021/172300
PCT Pub. Date: Sep. 2, 2021

(65) Prior Publication Data
US 2023/0098716 A1    Mar. 30, 2023

(30) Foreign Application Priority Data
Feb. 28, 2020   (JP) .................. 2020-034018

(51) Int. Cl.
| | |
|---|---|
| *C07C 233/11* | (2006.01) |
| *C07C 231/12* | (2006.01) |
| *C08K 5/20* | (2006.01) |

(52) U.S. Cl.
CPC .......... *C07C 233/11* (2013.01); *C07C 231/12* (2013.01); *C08K 5/20* (2013.01); *C07C 2603/18* (2017.05)

(58) Field of Classification Search
CPC ........ C07C 233/11; C07C 231/12; C08K 2/20
See application file for complete search history.

(56) References Cited

U.S. PATENT DOCUMENTS 2,299,948 A    10/1942   Bruson
11,760,717 B2   9/2023   Ouchi et al.

FOREIGN PATENT DOCUMENTS

| CN | 106905200 A | * 6/2017 | ......... G01N 21/6486 |
|---|---|---|---|
| EP | 4 089 069 | 11/2022 | |

(Continued)

OTHER PUBLICATIONS

English machine translation of CN 106905200A. (Year: 2017).*

(Continued)

*Primary Examiner* — John E Uselding
(74) *Attorney, Agent, or Firm* — Wenderoth, Lind & Ponack, L.L.P.

(57) ABSTRACT

The fluorene derivative of the present disclosure is represented by the following formula (1):

Wherein $R^1$ represents a substituent, k denotes an integer of 0 to 8, $R^{2a}$, $R^{2b}$, $R^{2c}$, and $R^{2d}$ each represent a hydrogen atom or a substituent, $R^{3a}$ and $R^{3b}$ each represent a hydrogen (Continued)

atom or a substituent, and $X^{1a}$ and $X^{1b}$ each represent a group defined in the following formula (X1):

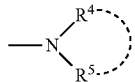

(X1)

wherein $R^4$ and $R^5$ each represent a hydrogen atom or an aliphatic hydrocarbon group, provided that the case where both $R^4$ and $R^5$ are a hydrogen atom is excluded; or $R^4$ and $R^5$ bond together to form a heterocyclic ring containing the nitrogen atom adjacent to $R^4$ and $R^5$. The present disclosure provides a novel fluorene derivative useful as an additive for improving the properties of a resin, a method for producing the same and a use thereof.

7 Claims, 4 Drawing Sheets

(56) References Cited

FOREIGN PATENT DOCUMENTS

| | | |
|---|---|---|
| JP | 2009-139214 | 6/2009 |
| JP | 2019-108311 | 7/2019 |
| KP | 10-2595411 | 10/2023 |
| WO | 2017/026250 | 2/2017 |

OTHER PUBLICATIONS

English machine translation of JP 2009-139214A (Year: 2009).*
International Search Report (ISR) issued May 11, 2021 in International (PCT) Application No. PCT/JP2021/006717.
Extended European Search Report issued Jul. 19, 2023 in corresponding European Patent Application No. 21760229.1.
Kretov et al., "Preparation of 9,9-bis (.beta.-cyanoethyl)fluorene and its derivatives from technical fluorene", Zhurnal Prikladnoi Khimii (Sankt-Peterburg, Russian Federation), 34, pp. 1386-1389, Coden: ZPKHAB; ISSN: 0044-4618, 1961, with abstract from Chemical Abstracts Service, XP002809419.
International Preliminary Report on Patentability and Written Opinion of the International Searching Authority issued Aug. 30, 2022 in International (PCT) Application No. PCT/JP2021/006717.
Communication pursuant to Article 94(3) EPC issued May 10, 2024, in corresponding European Patent Application No. 21760229.1.
IUPAC: "aryl groups : Gold Book" In: "IUPAC Compendium of Chemical Terminology", Jun. 2009, IUPAC, Research Triangle Park, NC, XP055460338, ISBN: 978-0-9678550-9-7, DOI: 10.1351/goldbook.A00464.
Request for the Submission of an Opinion issued Jun. 19, 2025 in corresponding Korean Patent Application No. 10-2022-7033218, with English language translation.

* cited by examiner

[Fig. 1]
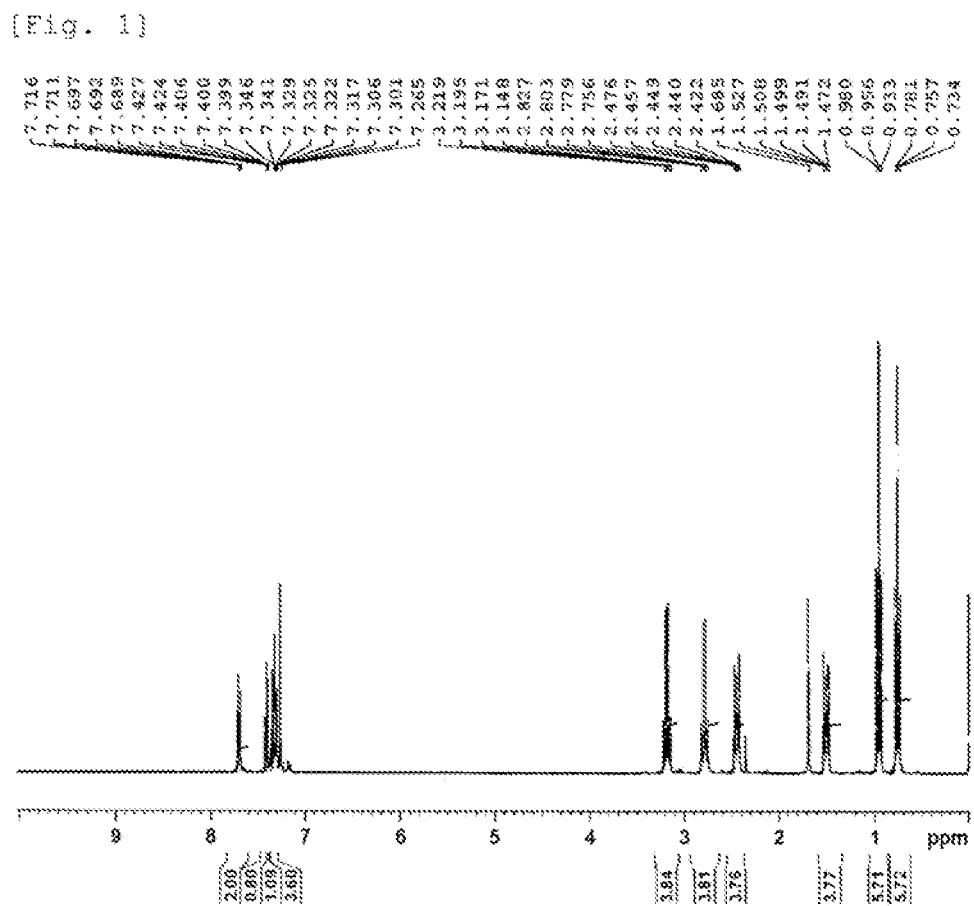

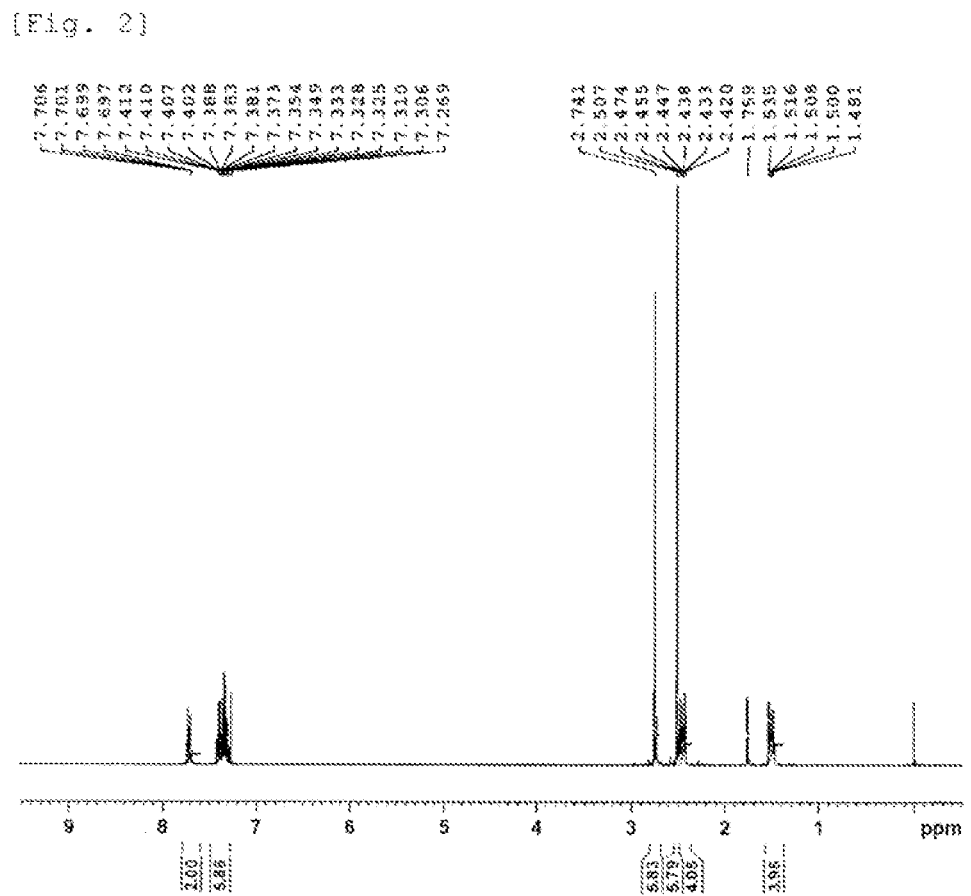
[Fig. 2]

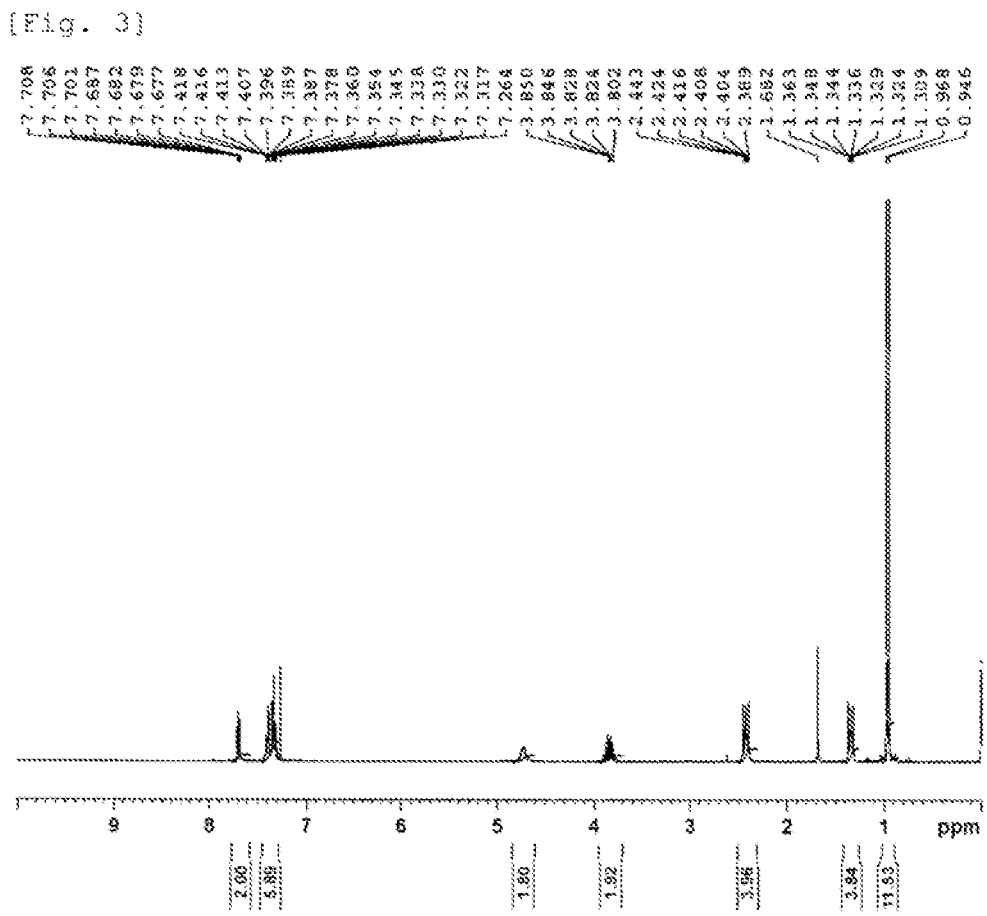
[Fig. 3]

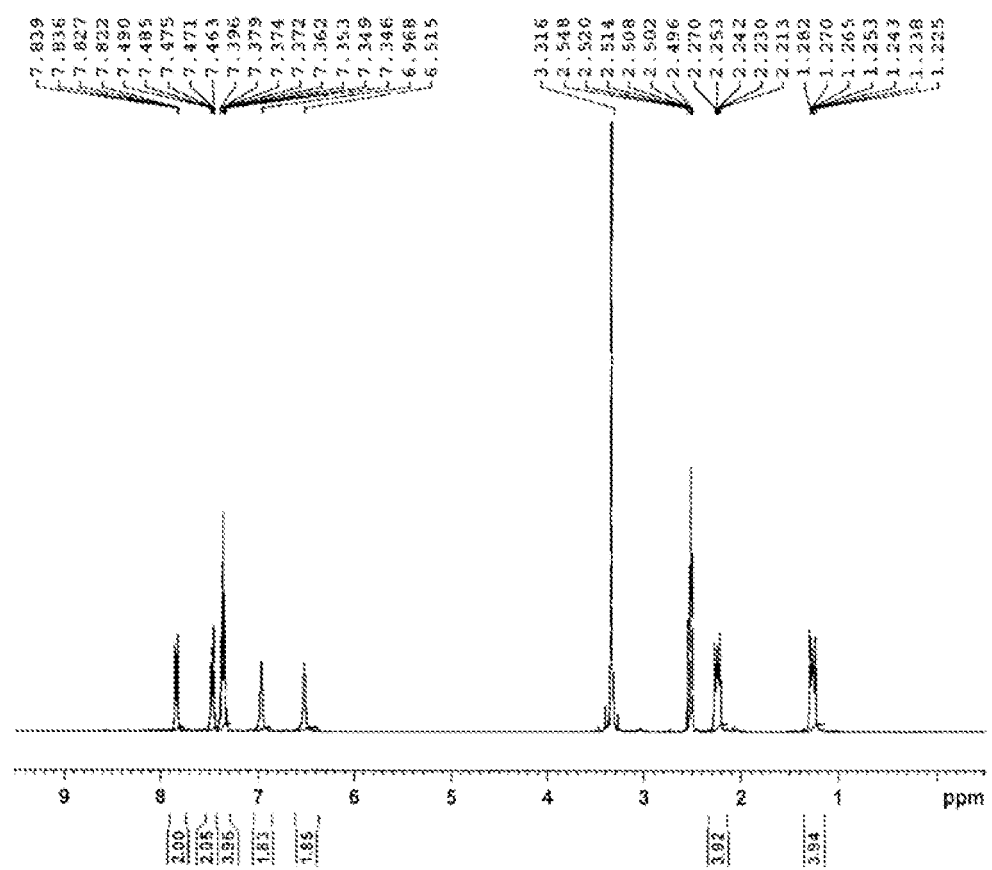

FLUORENE DERIVATIVE, AND PRODUCTION METHOD AND USE FOR SAME

TECHNICAL FIELD

The present disclosure relates to a novel fluorene derivative having an amide bond (or an amide group).

BACKGROUND ART

A fluorene derivative has been developed in various fields as a material for forming or producing an organic semiconductor, and an optical member, and other materials by utilizing excellent characteristics based on a specific chemical structure thereof, and is usually used as a monomer component for a resin. U.S. Pat. No. 2,299,948 (U.S. Pat. No. 2,299,948 A) (Patent Document 1) discloses that 9,9-di-(β-carbamoyl-ethyl)fluorene represented by the following formula is useful as an intermediate for preparing a synthetic resin.

[Chem. 1]

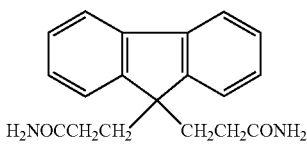

CITATION LIST

Patent Literature

Patent Document 1: U.S. Pat. No. 2,299,948 (U.S. Pat. No. 2,299,948 A)

SUMMARY OF INVENTION

Technical Problem

In Examples of Patent Document 1, the above-mentioned 9,9-di-(β-carbamoyl-ethyl)fluorene is prepared by reacting 9,9-di-(β-cyanoethyl)fluorene with sulfuric acid under predetermined conditions.

However, Patent Document 1 neither describe a compound in which the nitrogen atom constituting the amide group is substituted or bonded with a predetermined substituent, nor disclose or suggest the use of 9,9-di-(β-carbamoyl-ethyl)fluorene as an additive for improving the properties of the resin.

It is therefore an object of the present disclosure to provide a novel fluorene derivative useful as an additive for improving properties or characteristics of a resin, a method for producing the same and a use (or application) thereof.

Solution to Problem

The inventor of the present invention made intensive studies to achieve the above object and finally found that a fluorene derivative with a specific chemical structure is useful as a resin additive (a resin modifier). The present invention was accomplished based on the above findings.

That is, the fluorene derivative of the present disclosure is represented by the following formula (1):

[Chem. 2]

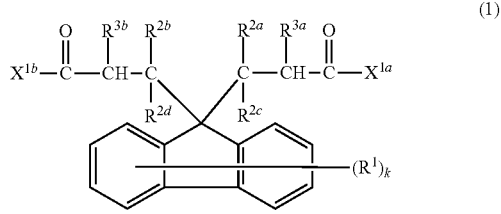

wherein $R^1$ represents a substituent, k denotes an integer of 0 to 8, $R^{2a}$, $R^{2b}$, $R^{2c}$, and $R^{2d}$ independently represent a hydrogen atom or a substituent, $R^{3a}$ and $R^{3b}$ independently represent a hydrogen atom or a substituent, and $X^{1a}$ and $X^{1b}$ independently represent a group defined in the following formula (X1):

[Chem. 3]

wherein $R^4$ and $R^5$ independently represent a hydrogen atom or an aliphatic hydrocarbon group, provided that the case where both $R^4$ and $R^5$ represent a hydrogen atom is excluded; or $R^4$ and $R^5$ bond together to form a heterocyclic ring containing the nitrogen atom adjacent to $R^4$ and $R^5$.

In the formula (1), $R^{2a}$ and $R^{2b}$ each may represent a hydrogen atom or a hydrocarbon group, $R^{2c}$ and $R^{2d}$ each may represent a hydrogen atom, $R^{3a}$ and $R^{3b}$ each may represent a hydrogen atom or a hydrocarbon group, $R^4$ and $R^5$ each may represent a hydrogen atom or an alkyl group, and $R^4$ and $R^5$ may bond together to form a heterocyclic ring, and the heterocyclic ring may be a 5- to 7-membered heterocyclic ring which may further contain at least one hetero atom selected from the group consisting of a nitrogen atom, an oxygen atom, and a sulfur atom.

In the formula (1), $R^{2a}$, $R^{2b}$, $R^{2c}$, and $R^{2d}$ each may represent a hydrogen atom, $R^{3a}$ and $R^{3b}$ each may represent a hydrogen atom or methyl group, $R^4$ and $R^5$ each may represent a hydrogen atom or a $C_{1-6}$alkyl group, and $R^4$ and $R^5$ may bond together to form a heterocyclic ring, and the heterocyclic ring may be a pyrrolidine ring, a piperidine ring, a homopiperidine ring, or a morpholine ring.

The present disclosure includes a method for producing a compound represented by the formula (1). According to this process, the method comprises or includes allowing a compound represented by the following formula (2) to react with compounds represented by the following formulae (3a) and (3b).

[Chem. 4]

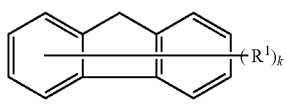
(2)

In the formula (2), $R^1$ and k each have the same meanings as defined in the formula (1).

[Chem. 5]

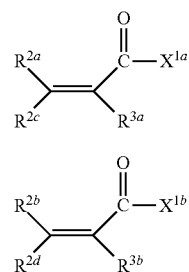

In the formulae (3a) and (3b), $R^{2a}$, $R^{2b}$, $R^{2c}$, and $R^{2d}$, $R^{3a}$ and $R^{3b}$, and $X^{1a}$ and $X^{1b}$ each have the same meanings as defined in the formula (1).

Further, the present disclosure includes a resin composition containing a compound represented by the formula (1) and a resin. The resin may be a thermoplastic resin. The resin may contain at least one resin selected from a polyolefinic resin and a polyamide-series resin. In the resin composition, a mass ratio of the compound represented by the formula (1) relative to the resin may be about 1/99 to 10/90 in terms of the former/the latter.

Furthermore, the present disclosure includes a method for improving a fluidity of a resin composition (or a resin), which comprises or includes adding a compound represented by the formula (1) to the resin such as a thermoplastic resin; and a fluidity improving agent improving the fluidity of the resin, and the fluidity improving agent comprises or includes the compound represented by the formula (1). The present disclosure includes a crystal of the compound represented by the formula (1).

In this description and claims, the number of carbon atoms in a substituent may be represented as $C_1$, $C_6$, $C_{10}$. For example, an alkyl group having one carbon atom is represented as "$C_1$alkyl group", and an aryl group having 6 to 10 carbon atoms is represented as "$C_{6-10}$aryl group".

Advantageous Effects of Invention

The novel fluorene derivative of the present disclosure is useful as an additive for modifying a resin. Specifically, the fluorene derivative can be used as a strength improving agent (a mechanical characteristic improving agent) for the resin, a fluidity improving agent, and other agents. The fluorene derivative has a high 5% mass reduction temperature, and therefore can effectively function as the additive while preventing or suppressing a thermal decomposition thereof even in a relatively high-temperature environment. The fluorene derivative has also an excellent solubility in solvents, and are easy to handle, and can be effectively dispersed in the resin.

BRIEF DESCRIPTION OF DRAWINGS

FIG. 1 is a $^1$H-NMR spectrum of DEAA-FL obtained in Example 1.
FIG. 2 is a ill-NMR spectrum of DMAA-FL obtained in Example 2.
FIG. 3 is a $^1$H-NMR spectrum of NIPAM-FL obtained in Example 3.
FIG. 4 is a $^1$H-NMR spectrum of AAD-FL obtained in Comparative Example 1.

DESCRIPTION OF EMBODIMENTS

[Fluorene Derivative]

The novel fluorene derivative of the present disclosure is a compound represented by the following formula (1).

[Chem. 6]

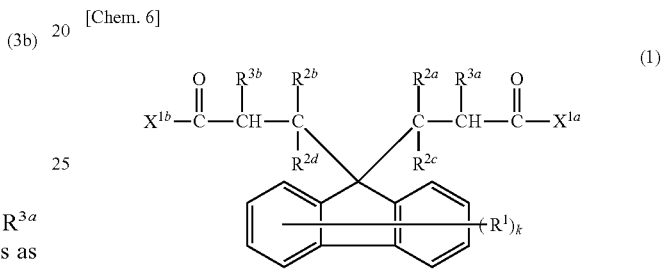
(1)

In the formula (1), $R^1$ represents a substituent, k denotes an integer of 0 to 8,
$R^{2a}$, $R^{2b}$, $R^{2c}$, and $R^{2d}$ independently represent a hydrogen atom or a substituent,
$R^{3a}$ and $R^{3b}$ independently represent a hydrogen atom or a substituent, and
$X^{1a}$ and $X^{1b}$ independently represent a group defined in the following formula (X1):

[Chem. 7]

(X1)

wherein $R^4$ and $R^5$ independently represent a hydrogen atom or an aliphatic hydrocarbon group, provided that the case where both $R^4$ and $R^5$ represent a hydrogen atom is excluded; or $R^4$ and $R^5$ bond together to form a heterocyclic ring containing the nitrogen atom adjacent to $R^4$ and $R^5$.

In the formula (1), the group $R^1$ may be a non-reactive substituent inert or inactive to a reaction, and may include, for example, a cyano group; a halogen atom such as a fluorine atom, a chlorine atom, and a bromine atom; and a hydrocarbon group such as an alkyl group and an aryl group. The aryl group may include a $C_{6-10}$aryl group such as phenyl group. The preferred group $R^1$ includes the cyano group, the halogen atom, or the alkyl group, and particularly the alkyl group.

The alkyl group may include, for example, a $C_{1-12}$alkyl group such as methyl group, ethyl group, n-propyl group, isopropyl group, n-butyl group, and t-butyl group, preferably a $C_{1-8}$alkyl group, and particularly a $C_{1-4}$alkyl group such as methyl group.

In a case where the substitution number k of the groups $R^1$ denotes the plural (2 or more), among the two benzene rings constituting the fluorene ring, the species of the two or more groups $R^1$ bonded to one or the other of the two benzene rings may be the same or different from each other; and the species of the two or more groups $R^1$ bonded to each of the two benzene rings may be the same or different from each other. The bonding position(s) (substitution position(s)) of the group(s) $R^1$ is any one of 1- to 8-positions of the fluorene ring without particular limitation, and may for example be 2-position, 7-position, and 2,7-positions of the fluorene ring.

The substitution number k may for example be an integer of about 0 to 6, and a preferred range of the substitution number k is an integer of 0 to 4, an integer of 0 to 3, and an integer of 0 to 2 in a stepwise manner. The substitution number k is more preferably 0 or 1, and particularly 0. Each substitution number of the groups $R^1$ on the two benzene rings constituting the fluorene ring may be different from each other, and the same substitution numbers are preferred.

The substituent represented by $R^{2a}$, $R^{2b}$, $R^{2c}$, and $R^{2d}$ may be a non-reactive substituent inert or inactive to a reaction, and may include, for example, a hydrocarbon group such as an alkyl group, a cycloalkyl group, an aryl group, and an aralkyl group.

The alkyl group may include, for example, a straight- or branched-chain $C_{1-10}$alkyl group such as methyl group, ethyl group, propyl group, isopropyl group, n-butyl group, isobutyl group, s-butyl group, and t-butyl group. The alkyl group is preferably a straight- or branched-chain $C_{1-6}$alkyl group, and more preferably a straight- or branched-chain $C_{1-4}$alkyl group.

Examples of the cycloalkyl group may include a $C_{5-10}$cycloalkyl group such as cyclopentyl group and cyclohexyl group.

The aryl group may include, for example, a $C_{6-12}$aryl group such as phenyl group, an alkylphenyl group, biphenylyl group, and naphthyl group. Examples of the alkylphenyl group may include a mono- to tri-$C_{1-4}$alkyl-phenyl group such as methylphenyl group (or tolyl group) and dimethylphenyl group (or xylyl group).

The aralkyl group may include, for example, a $C_{6-10}$aryl-$C_{1-4}$alkyl group such as benzyl group and phenethyl group.

The preferred substituent represented by $R^{2a}$, $R^{2b}$, $R^{2c}$, and $R^{2d}$ may include an alkyl group. The alkyl group is preferably a $C_{1-6}$alkyl group, a $C_{1-5}$alkyl group, a $C_{1-4}$alkyl group, and a $C_{1-3}$alkyl group in a stepwise manner, more preferably a $C_{1-2}$alkyl group, and particularly methyl group.

Each of the substituents $R^{2a}$, $R^{2b}$, $R^{2c}$, and $R^{2d}$ preferably represents a hydrogen atom or a hydrocarbon group, more preferably a hydrogen atom or an alkyl group, and further preferably a hydrogen atom. At least $R^{2c}$ and $R^{2d}$ each preferably represent a hydrogen atom; and $R^{2a}$ and $R^{2b}$ each in such an embodiment of $R^{2c}$ and $R^{2d}$ preferably represent a hydrogen atom or a hydrocarbon group, more preferably a hydrogen atom or an alkyl group, and particularly a hydrogen atom (that is, in particularly preferred embodiment, all $R^{2a}$, $R^{2b}$, $R^{2c}$, and $R^{2d}$ represent a hydrogen atom).

The species of the groups $R^{2a}$, $R^{2b}$, $R^{2c}$, and $R^{2d}$ may be different from each other; and the groups $R^{2a}$ and $R^{2b}$ are preferably the same species, and the groups $R^{2c}$ and $R^{2d}$ are preferably the same species.

The substituent represented by $R^{3a}$ and $R^{3b}$ may be a non-reactive substituent inert to a reaction, and may include, for example, a hydrocarbon group such as an alkyl group, a cycloalkyl group, an aryl group, and an aralkyl group. Such a hydrocarbon group may include, for example, the same hydrocarbon groups exemplified as the substituent represented by $R^{2a}$ and $R^{2b}$.

Among the substituents represented by $R^{3a}$ and $R^{3b}$, the preferred substituent is an alkyl group. The alkyl group is preferably a $C_{1-6}$alkyl group, a $C_{1-8}$alkyl group, a $C_{1-4}$alkyl group, and a $C_{1-3}$alkyl group in a stepwise manner, more preferably a $C_{1-2}$alkyl group, and particularly methyl group.

The group represented by $R^{3a}$ and $R^{3b}$ is preferably a hydrogen atom or an alkyl group, more preferably a hydrogen atom or methyl group, and particularly a hydrogen atom.

In the groups $X^{1a}$ and $X^{1b}$ (or formula (X1)), examples of the aliphatic hydrocarbon group represented by $R^4$ and $R^5$ may include an alkyl group, a cycloalkyl group, and a group of a combination of these groups.

The alkyl group may include, for example, a straight- or branched-chain $C_{1-12}$alkyl group such as methyl group, ethyl group, propyl group, isopropyl group, n-butyl group, isobutyl group, s-butyl group, t-butyl group, pentyl group, neopentyl group, hexyl group, octyl group, and decyl group.

Examples of the cycloalkyl group may include a $C_{5-10}$cycloalkyl group such as cyclopentyl group and cyclohexyl group.

Among the aliphatic hydrocarbon groups represented by $R^4$ and $R^5$, the aliphatic hydrocarbon group is preferably a straight- or branched-chain alkyl group, and more preferably a straight- or branched-chain $C_{1-8}$alkyl group, a straight- or branched-chain $C_{1-6}$alkyl group, and a straight- or branched-chain $C_{1-4}$alkyl group in a stepwise manner, and particularly a straight- or branched-chain $C_{1-3}$alkyl group such as methyl group, ethyl group, and isopropyl group. From a viewpoint of exhibiting higher dispersibility (or compatibility) for a resin, the aliphatic hydrocarbon group is preferably a straight- or branched-chain $C_{2-4}$alkyl group, and more preferably a straight- or branched-chain $C_{2-3}$alkyl group. In a case where both $R^4$ and $R^5$ represent an aliphatic hydrocarbon group, the species of $R^4$ and $R^5$ may be different from each other, and the same species are preferred.

The groups $R^4$ and $R^5$ may bond together to form a heterocyclic ring containing the nitrogen atom adjacent to $R^4$ and $R^5$ (N-containing heterocyclic ring or a nitrogen-atom-containing heterocyclic ring); said nitrogen atom, as a hetero atom, forms an amide group (carboxyamide) by combining $R^4$, $R^5$ with the carbonyl group; and if necessary, the heterocyclic ring may further contain, in addition to the nitrogen atom, 1 or more hetero atom(s) which may include, for example, a nitrogen atom, an oxygen atom, and a sulfur atom. The heterocyclic ring may contain at least one additional hetero atom selected from these hetero atoms, and preferably includes at least an oxygen atom. The number of hetero atoms constituting the heterocyclic ring may for example be about 1 to 3, and is preferably 1 to 2, and more preferably 2. Usually, the heterocyclic ring is, for example, a 5- to 7-membered ring (a 5- to 7-membered heterocyclic ring), preferably a 5- or 6-membered ring, and more preferably a 6-membered ring. The heterocyclic ring may be an aromatic heterocyclic ring, and is preferably a nonaromatic heterocyclic ring.

Representative examples of the heterocyclic ring may include a heterocyclic ring containing 1 or more nitrogen atom(s) such as a pyrrolidine ring, a piperidine ring, and a homopiperidine ring (an azepane ring, a hexahydroazepine ring, or hexamethyleneimine ring), and a heterocyclic ring containing a nitrogen atom and a hetero atom different from the nitrogen atom such as a morpholine ring; the heterocyclic ring is preferably a nonaromatic 5- to 7-membered heterocyclic ring containing a nitrogen atom and a hetero atom different from the nitrogen atom (particularly an oxygen atom) such as the morpholine ring.

In the formula (X1), with respect to the groups $R^4$ and $R^5$ adjacent to the nitrogen atom, one of the groups $R^4$ and $R^5$ may be a hydrogen atom, and the other may be an aliphatic hydrocarbon group; and both $R^4$ and $R^5$ may be an aliphatic hydrocarbon group; or $R^4$ and $R^5$ may bond together to form a heterocyclic ring. That is, a group $[—C(=O)—X^{1a}]$ and/or a group $[—C(=O)—X^{1b}]$ may be a mono-substituted amide group (or a N-substituted amide group); and a di-substituted amide group (or a N,N-disubstituted amide group). When the fluorene derivative is used as a resin additive, the group $[—C(=O)—X^{1a}]$ and/or the group $[—C(=O)—X^{1b}]$ is preferably the mono-substituted amide group in order to improve a fluidity, particularly a melt fluidity, and to effectively improve mechanical characteristics such as a flexural strength, a flexural modulus, a tensile strength, and a tensile modulus in a well-balanced manner. The group $[—C(=O)—X^{1a}]$ and/or the group $[—C(=O)—X^{1b}]$ is preferably the di-substituted amide group in order to extremely improve solubility of the fluorene derivative in solvents and to improve a fluidity further effectively, particularly a melt fluidity, by using the fluorene derivative as a resin additive. In the di-substituted amide group, both $R^4$ and $R^5$ are preferably the aliphatic hydrocarbon group. The species of the groups $X^{1a}$ and $X^{1b}$ may be different from each other, and the same species are preferred.

Representative examples of the compound represented by the formula (1) may include a compound in which each of $R^{2a}$, $R^{2b}$, $R^{2c}$, and $R^{2d}$ represents a hydrogen atom, each of $R^{3a}$ and $R^{3b}$ represents a hydrogen atom or methyl group, and one of $R^4$ and $R^5$ represents a hydrogen atom and the other represents an alkyl group in the formula (1), specifically a 9,9-bis[2-(N—$C_{1-6}$alkyl-carbamoyl)$C_{2-3}$alkyl]fluorene such as 9,9-bis[2-(N-methylcarbamoyl)ethyl]fluorene, 9,9-bis[2-(N-methylcarbamoyl)propyl]fluorene, 9,9-bis[2-(N-ethylcarbamoyl)ethyl]fluorene, 9,9-bis[2-(N-isopropylcarbamoyl)ethyl]fluorene, 9,9-bis[2-(N-isopropylcarbamoyl)propyl]fluorene, and 9,9-bis[2-(N-butylcarbamoyl)ethyl]fluorene; a compound in which each of $R^{2a}$, $R^{2b}$, $R^{2c}$, and $R^{2d}$ represents a hydrogen atom, each of $R^{3a}$ and $R^{3b}$ represents a hydrogen atom or methyl group, and each of $R^4$ and $R^5$ represents an alkyl group in the formula (1), specifically a 9,9-bis[2-(N,N-di$C_{1-6}$alkyl-carbamoyl)$C_{2-3}$alkyl] fluorene such as 9,9-bis[2-(N,N-dimethylcarbamoyl)ethyl] fluorene, 9,9-bis[2-(N,N-dimethylcarbamoyl)propyl] fluorene, 9,9-bis[2-(N,N-diethylcarbamoyl)ethyl]fluorene, 9,9-bis[2-(N,N-diethylcarbamoyl)propyl]fluorene, 9,9-bis [2-(N,N-diisopropylcarbamoyl)ethyl]fluorene, and 9,9-bis [2-(N,N-dibutylcarbamoyl)ethyl]fluorene; and a compound in which each of $R^{2a}$, $R^{2b}$, $R^{2c}$, and $R^{2d}$ represents a hydrogen atom, each of $R^{3a}$ and $R^{3b}$ represents a hydrogen atom or methyl group, and $R^4$ and $R^5$ bond together to form a 5- to 7-membered heterocyclic ring which may further contain, in addition to the nitrogen atom constituting an amide group, at least one hetero atom selected from the group consisting of a nitrogen atom, an oxygen atom, and a sulfur atom in the formula (1), specifically a 9,9-bis[2-(N-containing heterocyclic ring-N-yl-carbonyl)$C_{2-3}$alkyl]fluorene such as 9,9-bis[2-(morpholine-4-yl-carbonyl)ethyl] fluorene, 9,9-bis[2-(morpholine-4-yl-carbonyl)propyl] fluorene, 9,9-bis[2-(pyrrolidine-1-yl-carbonyl)ethyl] fluorene, 9,9-bis[2-(piperidine-1-yl-carbonyl)ethyl]fluorene, and 9,9-bis[2-(homopiperidine-1-yl-carbonyl)ethyl]fluorene.

Among these fluorene derivatives, the preferred fluorene derivatives are a compound in which each of $R^{2a}$, $R^{2b}$, $R^{2c}$, and $R^{2d}$ represents a hydrogen atom, each of $R^{3a}$ and $R^{3b}$ represents a hydrogen atom or methyl group, and one of the groups $R^4$ and $R^5$ in the groups $X^{1a}$ and $X^{1b}$ represents a hydrogen atom and the other represents an alkyl group in the formula (1) (N-alkyl substituted compound); and a compound in which each of $R^{2a}$, $R^{2b}$, $R^{2c}$, and $R^{2d}$ represents a hydrogen atom, each of $R^{3a}$ and $R^{3b}$ represents a hydrogen atom or methyl group, and both $R^4$ and $R^5$ in the groups $X^{1a}$ and $X^{1b}$ represent an alkyl group in the formula (1) (N,N-dialkyl substituted compound). Among such fluorene derivatives, the preferred fluorene derivative is the N-alkyl substituted compound such as a 9,9-bis[2-(N—$C_{1-4}$alkyl-carbamoyl)$C_{2-3}$alkyl]fluorene, and particularly a 9,9-bis[2-(N—$C_{2-4}$alkyl-carbamoyl)$C_{2-3}$alkyl]fluorene such as 9,9-bis [2-(N-isopropylcarbamoyl)ethyl]fluorene in order to improve the fluidity, particularly the melt fluidity by using the fluorene derivative as the resin additive, and to effectively improve mechanical characteristics such as the flexural strength, the flexural modulus, the tensile strength, and the tensile modulus in a well-balanced manner. The preferred fluorene derivative is the N,N-dialkyl substituted compound such as a 9,9-bis[2-(N,N-di$C^{1-4}$alkyl-carbamoyl)$C_{2-3}$alkyl]fluorene, more preferably a 9,9-bis[2-(N,N-di$C_{1-3}$alkyl-carbamoyl)$C_{2-3}$alkyl]fluorene such as 9,9-bis[2-(N,N-dimethylcarbamoyl)ethyl]fluorene and 9,9-bis[2-(N,N-diethylcarbamoyl)ethyl]fluorene, and particularly 9,9-bis[2-(N,N-diethylcarbamoyl)ethyl]fluorene in order to greatly improve a solubility of the fluorene derivative in a wide variety of solvents, and to further effectively improve a fluidity, particularly a melt fluidity by using the fluorene derivative as the resin additive.

[Method for Producing Fluorene Derivative]

The method for producing a compound represented by the formula (1) is not particularly limited to a specific method, and may for example be prepared by reacting a compound represented by the following formula (2) with compounds represented by the following formulae (3a) and (3b) (Michael addition reaction).

[Chem. 8]

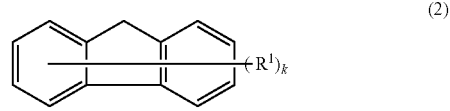

(2)

In the formula (2), $R^1$ and k, including preferred embodiments, each have the same meanings as defined in the formula (1).

[Chem. 9]

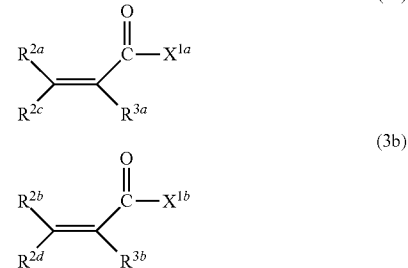

(3a)

(3b)

In the formulae (3a) and (3b), $R^{2a}$, $R^{2b}$, $R^{2c}$, and $R^{2d}$, $R^{3a}$ and $R^{3b}$, and $X^{1a}$ and $X^{1b}$, including preferred embodiments, each have the same meanings as defined in the formula (1).

Representative examples of the compound represented by the formula (2) may include 9H-fluorene.

Each of the compounds represented by the formulae (3a) and (3b) may be either E-isomer or Z-isomer depending on the species or kinds of the groups $R^{2a}$, $R^{2b}$, $R^{2c}$, and $R^{2d}$, $R^{3a}$ and $R^{3b}$, and $X^{1a}$ and $X^{1b}$.

Representative compounds represented by the formulae (3a) and (3b), for example, correspond to the compound specifically exemplified as a compound represented by the formula (1), and may include a compound in which each of $R^{2a}$, $R^{2b}$, $R^{2c}$, and $R^{2d}$ represents a hydrogen atom, each of $R^{3a}$ and $R^{3b}$ represents a hydrogen atom or methyl group, and one of the groups $R^4$ and $R^5$ represents a hydrogen atom and the other represents an alkyl group, specifically, for example, a N—$C_{1-6}$alkyl-(meth)acrylamide such as N-isopropyl(meth)acrylamide; a compound in which each of $R^{2a}$, $R^{2b}$, $R^{2c}$, and $R^{2d}$ represents a hydrogen atom, each of $R^{3a}$ and $R^{3b}$ represents a hydrogen atom or methyl group, and both $R^4$ and $R^5$ represent an alkyl group, specifically, for example, a N,N-di$C_{1-6}$alkyl-(meth)acrylamide such as N,N-dimetyl(meth)acrylamide and N,N-dietyl(meth)acrylamide; a compound in which each of $R^{2a}$, $R^{2b}$, $R^{2c}$, and $R^{2d}$ represents a hydrogen atom, each of $R^{3a}$ and $R^{3b}$ represents a hydrogen atom or methyl group, and $R^4$ and $R^5$ bond together to form a 5- to 7-membered heterocyclic ring which may further contain, in addition to the nitrogen atom constituting an amide group, at least one hetero atom selected from the group consisting of a nitrogen atom, an oxygen atom, and a sulfur atom, specifically, for example, a N-(meth)acryloyl N-containing heterocyclic ring such as N-(meth)acryloylmorpholine. The same compound is preferably used as the compound represented by the formula (3a) and the compound represented by the formula (3b).

The amount of the compound represented by the formula (2) relative to the total amount of the compounds represented by the formulae (3a) and (3b) may for example be a molar ratio of about 1/2 to 1/10 in terms of the former/the latter; and a preferred range of the molar ratio is, in terms of the former/the latter, 1/2 to 1/5, 1/2.01 to 1/3, and 1/2.03 to 1/2.1 in a stepwise manner.

The reaction may be carried out in the presence of a base. The base may include, for example, a metal hydroxide, a metal carbonate or bicarbonate (hydrogen carbonate), and a metal alkoxide.

Examples of the metal hydroxide may include an alkali metal hydroxide such as sodium hydroxide and potassium hydroxide; and an alkaline earth metal hydroxide such as barium hydroxide.

Examples of the metal carbonate or bicarbonate may include an alkali metal carbonate or bicarbonate such as sodium carbonate, potassium carbonate, and sodium bicarbonate (sodium hydrogen carbonate).

Examples of the metal alkoxide may include an alkali metal alkoxide such as sodium methoxide, sodium ethoxide, and potassium t-butoxide.

These bases may be used alone or in combination of two or more. Among these bases, the base is preferably the metal hydroxide, and more preferably the alkali metal hydroxide such as potassium hydroxide. The ratio of the bases may for example be about 0.001 to 0.1 mol, and is preferably 0.01 to 0.05 mol relative to 1 mol of the compound represented by the formula (2).

The reaction may be carried out in the presence or absence of phase transfer catalyst(s). The phase transfer catalyst may include, for example, a tetraalkylammonium halide such as tetrabutylammonium bromide (TBAB) and trioctylmethylammonium chloride. These phase transfer catalysts may be used alone or in combination of two or more. Among these phase transfer catalysts, TBAB is preferred. The ratio of the phase transfer catalysts may for example be about 0.001 to 0.1 mol, and is preferably 0.01 to 0.05 mol relative to 1 mol of the compound represented by the formula (2).

The reaction may be carried out in the absence or presence of an inert or inactive solvent to a reaction. Examples of the solvent may include water; an alcohol such as methanol and ethanol; an ether such as a cyclic ether and a chain ether; a sulfoxide such as dimethyl sulfoxide (DMSO); and a hydrocarbon such as an aliphatic hydrocarbon, an alicyclic hydrocarbon, and an aromatic hydrocarbon.

Examples of the cyclic ether may include 1,4-dioxane and tetrahydrofuran. Examples of the chain ether may include a dialkyl ether such as diethyl ether and diisopropyl ether; and a glycol ether. The glycol ether may include, for example, a (poly)alkylene glycol monoalkyl ether such as methyl cellosolve and methyl carbitol; and a (poly)alkylene glycol dialkyl ether such as dimethoxyethane.

Examples of the aliphatic hydrocarbon may include hexane and dodecane. The alicyclic hydrocarbon may include cyclohexane. The aromatic hydrocarbon may include, for example, toluene and xylene.

These solvents may be used alone or in combination of two or more. Among these solvents, the preferred solvent is a mixed solvent of water, the sulfoxide such as DMSO, and the aromatic hydrocarbon such as toluene. The water may be added in the form of an aqueous solution of the base described above. The amount of the solvents is not particularly limited to a specific amount as long as the progress of the reaction is not interfered. The amount of the solvents may for example be about 10 to 500 mL, and is preferably 50 to 200 mL relative to 100 g of the total amount of the compounds represented by the formulae (2), (3a), and (3b).

The reaction may be carried out in an atmosphere of an inert gas such as a nitrogen gas; and a rare or noble gas such as helium and argon. The reaction temperature is, for example, 50 to 200° C., and preferably 80 to 100° C. The reaction time is not particularly limited to a specific time, and may for example be about 0.5 to 10 hours.

After the completion of the reaction, if necessary, the reaction mixture may be subjected to a conventional separation and purification means, for example, a method such as neutralization, washing, extraction, filtration, decantation, concentration, dehydration, drying, crystallization, and chromatography and a combination of these methods.

For example, the produced fluorene derivative may be separated and purified by a recrystallization method. In the recrystallization method, as examples of the crystallization solvent, there may be mentioned an alcohol such as a lower alcohol, and preferably a $C_{1-4}$alcohol such as methanol and ethanol. Specifically, the alcohol may be added to an obtained or crude fluorene derivative, the mixture may be heated to about 50 to 100° C., and preferably 60 to 70° C. for dissolving, and then allowed to stand at about 10 to 30° C., and preferably about 20 to 25° C. to precipitate crystals.

[Characteristics and Application of Fluorene Derivative]
(Characteristics)

The fluorene derivative obtained as described above may be in a crystalline or amorphous form. In a crystalline fluorene derivative, the fluorene derivative in which the groups [—C(=O)—$X^{1a}$] and [—C(=O)—$X^{1b}$] each are the mono-substituted amide group, may have a melt point of, for example, about 150 to 300° C., and the melting point is preferably 200 to 270° C., and more preferably 220 to 250° C.; and the fluorene derivative in which the groups [—C(=O)—X$^{1a}$] and [—C(=O)—X$^{1b}$] each are the di-substituted amide group, may have a melt point of, for example, about 50 to 200° C., and the melting point is preferably 70 to 180° C., and more preferably 80 to 160° C.

Further, a 5% mass reduction temperature of the fluorene derivative may for example be about 200 to 350° C., and is preferably 230 to 330° C., 240 to 320° C., 250 to 310° C., 270 to 305° C., and 290 to 300° C. in a stepwise manner. The fluorene derivative has a high heat resistance as described above. Therefore, even in a high-temperature environment, the fluorene derivative can be effectively used as a resin additive.

The fluorene derivative has an excellent solubility in solvents. In particular, a compound (the fluorene derivative) in which the group [—C(=O)—X$^{1a}$] and/or [—C(=O)—X$^{1b}$] are the di-substituted amide group in the formula (1) tends to dissolve in more variety of solvents.

In this description and claims, the melting point, the 5% mass reduction temperature, and the solubility in solvents can be measured according to the methods described in Examples mentioned below.

(Applications)

The fluorene derivative represented by the formula (1) can be effectively used as a resin additive for improving the properties of a resin by adding to the resin, for example, as a fluidity improving agent improving a fluidity, particularly a melt fluidity, and a strength improving agent improving mechanical properties or characteristics such as a flexural strength, a flexural modulus, a tensile strength, and a tensile modulus. The fluorene derivative may be added alone or in combination of two or more.

The resin may be a curable resin (thermosetting resin or photo (light) curable resin), or a thermoplastic resin.

The curable resin may include, for example, a phenolic resin such as a resol phenolic resin and a novolac or novolak phenolic resin; an amino resin such as a urea resin, a melamine resin, and a guanamine resin; a furan resin; an unsaturated polyester resin; a diallyl phthalate resin; a vinyl ester resin (or an epoxy (meth)acrylate resin); a polyfunctional (meth)acrylate-series resin; an epoxy resin; an urethane resin; a polyimide resin such as a bismaleimide-series resin; and a silicone resin.

The thermoplastic resin may include, for example, a polyolefinic resin, a styrenic resin, a (meth)acrylic resin, a vinyl acetate-series resin, a vinyl chloride-series resin, a fluororesin, a polyester-series resin, a polycarbonate-series resin (PC), a polyamide-series resin (PA), a polyacetal resin (POM), a poly(phenylene ether) resin (PPE), a polyetherketone-series resin, a phenoxy resin, a polyketone resin, a poly(phenylene sulfide) resin (PPS), a polysulfone-series resin, a cellulose derivative, a thermoplastic polyimide resin, a polyethernitrile resin, and a thermoplastic elastomer (TPE).

The polyolefinic resin may include, for example, a chain or liner olefinic resin such as a polyethylene-series resin and a polypropylene-series resin; and a cylic olefinic resin.

The styrenic resin may include, for example, a polystyrene (PS) such as a general-purpose polystyrene (GPPS) and a syndiotactic polystyrene (SPS); and a styrenic copolymer. Examples of the styrenic copolymer may include a styrene-methyl (meth)acrylate copolymer (MS resin), a styrene-acrylonitrile copolymer (AS resin), and a rubber component-containing styrenic resin or rubber graft styrenic copolymer. The rubber component-containing styrenic resin or rubber graft styrenic copolymer may include, for example, a high impact polystyrene (HIPS), an acrylonitrile-butadiene-styrene copolymer (ABS resin), an AXS resin, and a methyl methacrylate-butadiene-styrene copolymer (MBS resin). The AXS resin may include, for example, an acrylonitrile-acrylic rubber-styrene copolymer (AAS resin), an acrylonitrile-chlorinated polyethylene-styrene copolymer (ACS resin), and an acrylonitrile-(ethylene-propylene-diene rubber)-styrene copolymer (AES resin).

Examples of the (meth)acrylic resin may include a homo- or co-polymer of a (meth)acrylic monomer such as poly(methyl methacrylate) (PMMA) and a (meth)acrylic acid-(meth)acrylate copolymer.

Examples of the vinyl acetate-series resin may include a poly(vinyl acetate) (PVAc), a poly(vinyl alcohol) (PVA), and a poly(vinyl acetal). The poly(vinyl acetal) may include, for example, a poly(vinyl formal) (PVF) and a poly(vinyl butyral) (PVB).

Examples of the vinyl chloride-series resin may include a vinyl chloride resin and a vinylidene chloride resin. The vinyl chloride resin may include, for example, a vinyl chloride homopolymer (PVC); a vinyl chloride copolymer such as a vinyl chloride-vinyl acetate copolymer. The vinylidene chloride resin may include, for example, a vinylidene chloride copolymer such as a vinylidene chloride-vinyl chloride copolymer and a vinylidene chloride-acrylonitrile copolymer.

Examples of the fluororesin may include a polytetrafluoroethylene (PTFE), a poly(chlorotrifluoroethylene) (PCTFE), a poly(vinylidene fluoride) or poly(vinylidene difluoride) (PVDF), a poly(vinyl fluoride) (PVF), a tetrafluoroethylene-hexafluoropropylene copolymer (FEP), a tetrafluoroethylene-perfluoroalkyl vinyl ether copolymer (PFA), an ethylene-tetrafluoroethylene copolymer (ETFE), and an ethylene-chlorotrifluoroethylene copolymer (ECTFE).

Examples of the polyester-series resin may include a polyalkylene arylate-series resin, a polyarylate-series resin, and a liquid crystal polyester (LCP). The polyalkylene arylate-series resin may include, for example, a poly(ethylene terephthalate) (PET), a poly(trimethylene terephthalate) (PTT), a poly(butylene terephthalate) (PBT), a poly(1,4-cyclohexyldimethylene terephthalate) (PCT), and a poly(ethylene naphthalate).

Examples of the polycarbonate-series resin (PC) may include a bisphenol polycarbonate-series resin such as a bisphenol A polycarbonate-series resin.

Examples of the polyamide-series resin (PA) may include an aliphatic polyamide resin such as polyamide 6 and polyamide 66; an aromatic polyamide resin or an aramid resin such as poly m-phenyleneisophthalamide and poly p-phenyleneterephthalamide.

Examples of the polyetherketone-series resin may include a polyetherketone resin (PEK), a polyetheretherketone resin (PEEK), and a polyetherketoneetherketoneketone (PEKEKK).

Examples of the polyketone resin may include an aliphatic polyketone resin.

Examples of the polysulfone-series resin may include a polysulfone resin (PSF) and a polyethersulfone (PES).

Examples of the cellulose derivative may include a cellulose ester such as a nitrocellulose, a cellulose acetate, and a cellulose acetate propionate; and a cellulose ether such as an ethyl cellulose.

Examples of the thermoplastic polyimide resin may include a polyetherimide (PEI) and a polyamideimide.

Examples of the thermoplastic elastomer (TPE) may include a polystyrenic TPE, a polyolefinic TPE (TPO), a polydiene-series TPE, a chlorine-series TPE, a fluorine-series TPE, a polyurethane-series TPE (TPU), a polyester-series TPE (TPEE), and a polyamide-series TPE (TPA).

These resins may be used alone or in combination of two or more. Among these resins, the resin is preferably the thermoplastic resin, more preferably the polyolefinic resin such as the polyethylene-series resin and the polypropylene-series resin, and the polyamide-series resin, for effectively improving characteristics of the resin.

The polyolefinic resin may include, for example, a chain or liner olefinic resin containing α-olefin as a main polymerization component; a cyclic olefinic resin containing a cyclic olefin as a polymerization component. The cyclic olefinic resin may include, for example, a cyclic olefin copolymer (COC) such as an ethylene-norbornene copolymer; an addition polymer or ring-opening polymer of the cyclic olefin, or hydrogenated polymer thereof, such as polynorbornene, polydicyclopentadiene, polycyclopentadiene, or hydrogenated polymers thereof. These polyolefinic resins may be used alone or in combination of two or more. Among these polyolefinic resins, the chain or liner olefinic resin is preferred.

The α-olefin, which is the polymerization component of the chain or liner olefinic resin, may include, for example, an α-$C_{2-20}$olefin such as ethylene, propylene, 1-butene, 1-pentene, 3-methyl-1-butene, 1-hexene, 3-methyl-1-pentene, 4-methyl-1-pentene, 1-heptene, 4-methyl-1-hexene, 4,4-dimethyl-1-pentene, 3-ethyl-1-pentene, 1-octene, 4,4-dimethyl-1-hexene, 3-ethyl-1-hexene, 4-ethyl-1-hexene, 1-decene, 1-dodecene, 1-tetradecene, 1-hexadecene, 1-octadecene, and 1-eicosene, and is preferably an α-$C_{2-10}$olefin, and more preferably an α-$C_{2-6}$olefin such as ethylene and propylene.

The chain or liner olefinic resin may be a homopolymer or a copolymer obtained by using the α-olefin. The polymerization component in the copolymer may contain two or more kinds of α-olefins, or may contain a copolymerizable monomer different from the α-olefin. The copolymer may be a random copolymer, a block copolymer, and a graft copolymer.

Examples of the copolymerizable monomer different from the α-olefin may include a (meth)acrylic monomer, an unsaturated carboxylic acid or acid anhydride thereof, a vinyl carboxylate (a vinyl carboxylic acid ester), and a diene.

The (meth)acrylic monomer may include, for example, (meth)acrylic acid; (meth)acrylic ester or (meth)acrylate; (meth)acrylamide; a N-substituted (meth)acrylamide; and (meth)acrylonitrile. Examples of the (meth)acrylic ester may include a (meth)acrylic alkyl ester and a glycidyl (meth)acrylate. Examples of the (meth)acrylic alkyl ester may include a (meth)acrylic $C_{1-10}$alkyl ester such as methyl (meth)acrylate and ethyl (meth)acrylate. Examples of the N-substituted (meth)acrylamide may include a mono- or di-alkyl (meth)acrylamide such as N,N-dimethyl (meth)acrylamide and N-isopropyl (meth)acrylamide.

The unsaturated carboxylic acid or acid anhydride thereof may include, for example, (meth)acrylic acid, maleic acid, fumaric acid, itaconic acid, citraconic acid, crotonic acid, isocrotonic acid, mesaconic acid, angelic acid, or anhydrides thereof (e.g., maleic acid anhydride).

The vinyl carboxylate may include a vinyl ester of a saturated carboxylic acid such as vinyl acetate and vinyl propionate.

The diene may include, for example, an unconjugated alkadiene such as 1,4-hexadiene, 1,7-octadiene, 4-methyl-1,4-hexadiene, and 5-methyl-1,4-hexadiene; and a conjugated alkadiene such as butadiene and isoprene.

These copolymerizable monomers may be used alone or in combination of two or more. When the chain or liner olefinic resin comprises a unit of the copolymerizable monomer, a proportion of the copolymerizable monomer unit(s) in total constitutional units of the chain olefinic resin may for example be about not more than 90 mol %, and is preferably not more than 70 mol %, not more than 50 mol %, not more than 30 mol %, not more than 20 mol %, and not more than 10 mol % in a stepwise manner. The proportion of the copolymerizable monomer unit in total constitutional units of the chain olefinic resin is for example 0.01 to 30 mol %, and preferably 0.1 to 20 mol %, and 1 to 10 mol % in a stepwise manner.

Representative examples of the chain or liner olefinic resin may include a poly α-$C_{2-6}$olefinic resin such as a polyethylene-series resin, a polypropylene-series resin, poly (1-butene)-series resin, and poly (4-methyl-1-pentene)-series resin. These polyolefinic resins may be used alone or in combination of two or more. Among these polyolefinic resins, the polyethylene-series resin and the polypropylene resin are preferred.

The polyethylene-series resin may include, for example, a low-density polyethylene (LDPE), a medium-density polyethylene (MDPE), a high-density polyethylene (HDPE), a linear low-density polyethylene (LLDPE), an ultra-high molecular weight polyethylene (UHMWPE), an ethylene-(α-$C_{3-10}$olefin) copolymer, a modified polyethylene, a chlorinated polyethylene, and an ionomer. Examples of the ethylene-(α-$C_{3-10}$olefin) copolymer may include an ethylene-propylene copolymer, an ethylene-(1-butene) copolymer, an ethylene-propylene-(1-butene) copolymer, and an ethylene-(4-methyl-1-pentene) copolymer. Examples of the modified polyethylene may include a maleic anhydride modified polyethylene.

The polyethylene-series resin may be produced by using a multi-site catalyst such as Ziegler catalyst, or a single-site catalyst such as a metallocene catalyst, and preferably by using the metallocene catalyst.

These polyethylene-series resins may be used alone or in combination of two or more. Among these polyethylene-series resins, the ethylene-(α-$C_{3-10}$olefin) copolymer is preferred, and more preferably the ethylene-(α-$C_{3-10}$olefin) copolymer produced by using the metallocene catalyst.

The density of the polyethylene-series resin may for example be selected from a range of about 0.87 to 1 g/cm$^3$, and a preferred range of the density of the polyethylene resin is 0.88 to 0.98 g/cm$^3$, 0.885 to 0.95 g/cm$^3$, 0.895 to 0.92 g/cm$^3$, and 0.9 to 0.91 g/cm$^3$ in a stepwise manner. In this description and claims, the density can be measured in accordance with JIS K 7122.

The weight-average molecular weight Mw of the polyethylene-series resin may for example be selected from a range of about 10000 to 10000000. The number-average molecular weight Mn of the polyethylene-series resin may for example be selected from a range of about 10000 to 1000000. The molecular weight distribution (Mw/Mn) may for example be selected from a range of about 1 to 50. In this description and claims, the weight-average molecular weight, the number-average molecular weight, and the molecular weight distribution may be measured by GPC in terms of standard polystyrene.

The melt frow rate (MFR) (unit: g/10 min) of the polyethylene-series resin may for example be about 1 to 50, and a preferred range of the MFR is 2 to 30, 3 to 25, 4 to 20, 5 to 18, 6 to 15, and 8 to 12 in a stepwise manner. In this description and claims, the MFR of the polyethylene-series resin can be measured in accordance with JIS K6922-2.

The polypropylene-series resin may be polypropylene (or propylene homopolymer); or a copolymer of propylene and another copolymerizable monomer, or a modified polypropylene. Examples of the copolymer of propylene and another copolymerizable monomer, or the modified polypropylene may include a copolymer of propylene and another $\alpha$-$C_{2-10}$olefin such as a propylene-ethylene copolymer, a propylene-(1-butene) copolymer, and a propylene-ethylene-(1-butene) copolymer; a maleic anhydride modified polypropylene; and a chlorinated polypropylene. The copolymer of propylene and another copolymerizable monomer, or the modified polypropylene may be a random copolymer, a block copolymer, or a graft copolymer. In the copolymer of propylene and another $\alpha$-$C_{2-10}$olefin, a proportion of the propylene (or propylene unit) in total monomers is for example not less than 70 mol %, and a preferred range of the proportion is preferably not less than 80 mol %, and not less than 90 mol % in a stepwise manner. The proportion of the propylene (or propylene unit) in total monomers is for example 75 to 99.5 mol %, and a preferred range of the proportion is 85 to 99 mol %, and 94 to 98 mol % in a stepwise manner.

The polypropylene-series resin may include, from a viewpoint of crystallinity, a high-density polypropylene (high crystallinity polypropylene (HCPP)), a medium-density polypropylene, a low-density polypropylene (low-crystallinity polypropylene (LCPP)), and a very- or ultra-low-density polypropylene (a very- or ultra-low-crystallinity polypropylene (VLCPP)). In view of stereoregularity, the polypropylene-series resin may be a polypropylene-series resin having stereoregularity such as an isotactic polypropylene (IPP) and a syndiotactic polypropylene (SPP), and may be a polypropylene-series resin having no stereoregularity such as an atactic polypropylene (APP). The polypropylene-series resin with stereoregularity may be a polypropylene-series resin having a narrow molecular weight distribution, obtained by using the metallocene catalyst.

These polypropylene-series resins may be used alone or in combination of two or more. Among these polypropylene-series resins, polypropylene (propylene homopolymer) is preferred.

The weight-average molecular weight Mw of the polypropylene-series resin may for example be selected from a range of about 10000 to 10000000. The number-average molecular weight Mn of the polypropylene-series resin may for example be selected from a range of about 10000 to 1000000. The molecular weight distribution (Mw/Mn) may for example be selected from a range of about 1 to 50. In this description and claims, the weight-average molecular weight, the number-average molecular weight, and the molecular weight distribution can be measured by GPC in terms of standard polystyrene.

The melt frow rate (MFR) (unit: g/10 min) of the polypropylene-series resin may for example be about 0.5 to 55, and a preferred range of the MFR is 1 to 50, 2 to 40, 3 to 30, 4 to 20, 5 to 15, 6 to 12, and 8 to 10 in a stepwise manner. In this description and claims, the MFR of the polypropylene-series resin can be measured in accordance with JIS K7210 under the condition of 230° C.

As a polyamide-series resin (PA), a conventional polyamide-series resin can be used. The polyamide-series resin may for example be formed with an aliphatic monomer component, an alicyclic monomer component, and/or an aromatic monomer component.

In this description and claims, a monomer component having a carboxyl group such as dicarboxylic acid described later, may be an amide-forming derivative, for example, an acid halide such as an acid chloride, and an acid anhydride.

The aliphatic monomer component may include, for example, an aliphatic diamine component, an aliphatic dicarboxylic acid component, an aliphatic aminocarboxylic acid component, and a lactam component.

The aliphatic diamine component may include, for example, a straight- or branched-chain $C_{2-20}$alkylene diamine such as tetramethylene diamine, hexamethylene diamine, 2-methyl pentamethylene diamine, nonamethylene diamine, 2-methyl octamethylene diamine, trimethyl hexamethylene diamine, decamethylene diamine, and dodecamethylene diamine, and is preferably a straight- or branched-chain $C_{4-16}$alkylene diamine, and more preferably a straight- or branched-chain $C_{6-12}$alkylene diamine.

Examples of the aliphatic dicarboxylic acid component may include a saturated aliphatic dicarboxylic acid (a straight- or branched-chain alkane dicarboxylic acid) and an unsaturated aliphatic dicarboxylic acid.

The straight- or branched-chain alkane dicarboxylic acid may include, for example, a straight- or branched-chain $C_{1-20}$alkane-dicarboxylic acid such as malonic acid, succinic acid, glutaric acid, adipic acid, pimelic acid, suberic acid, azelaic acid, sebacic acid, and 1,10-decane dicarboxylic acid, and is preferably a straight- or branched-chain $C_{2-16}$alkane-dicarboxylic acid, and more preferably a straight- or branched-chain $C_{4-12}$alkane-dicarboxylic acid such as adipic acid, sebacic acid, and 1,10-decane dicarboxylic acid.

The unsaturated aliphatic dicarboxylic acid may include, for example, a $C_{2-10}$alkene-dicarboxylic acid such as maleic acid, fumaric acid, and itaconic acid.

The aliphatic aminocarboxylic acid component may include, for example, an amino$C_{2-20}$alkyl-carboxylic acid such as 6-aminohexanoic acid, 11-aminoundecanoic acid, and 12-aminododecanoic acid, and is preferably an amino$C_{3-16}$alkyl-carboxylic acid, and more preferably an amino$C_{5-11}$alkyl-carboxylic acid.

The lactam component may be a lactam corresponding to the aliphatic aminocarboxylic acid; and may include, for example, a 4- to 13-membered ring lactam such as ε-caprolactam and ω-laurolactam, and preferably a 7- to 13-membered ring lactam.

The alicyclic monomer component has an alicyclic skeleton (or an aliphatic hydrocarbon ring skeleton), and may include, for example, an alicyclic diamine component, an alicyclic dicarboxylic acid component, and an alicyclic aminocarboxylic acid component.

Examples of the alicyclic diamine component may include a diaminocycloalkane, bis(aminoalkyl)cycloalkane, and bis(aminocyclohexyl)alkane.

The diaminocycloalkane may include, for example, a diamino$C_{5-10}$cycloalkane such as diaminocyclohexane.

The bis(aminoalkyl)cycloalkane may include, for example, a bis(amino$C_{1-4}$alkyl)$C_{5-10}$cycloalkane such as bis(aminomethyl)cyclohexane.

The bis(aminocyclohexyl)alkane may include, for example, a bis(aminocyclohexyl)$C_{1-6}$alkane such as bis(4-aminocyclohexyl)methane and 2,2-bis(4-aminocyclohexyl)propane; a bis(amino-mono- to tri-$C_{1-6}$alkyl-$C_{5-10}$cycloalkyl)$C_{1-6}$alkane such as bis(4-amino-3-methylcyclohexyl)methane, bis(4-amino-3,5-dimethylcyclohexyl)methane, and 2,2-bis(4-amino-3-methylcyclohexyl)propane.

Examples of the alicyclic dicarboxylic acid component may include a cycloalkanedicarboxylic acid, a bridged ring (crosslinked ring) cycloalkanedicarboxylic acid, a cycloalkenedicarboxylic acid, and a bridged ring (crosslinked-ring) cycloalkenedicarboxylic acid.

The cycloalkanedicarboxylic acid may include, for example, a $C_{5-10}$cycloalkane-dicarboxylic acid such as 1,4-cyclohexanedicarboxylic acid.

The bridged ring cycloalkanedicarboxylic acid may include, for example, a bi- or tri-cycloalkanedicarboxylic acid such as decalindicarboxylic acid, norbornanedicarboxylic acid, adamantanedicarboxylic acid, and tricyclodecanedicarboxylic acid.

The cycloalkenedicarboxylic acid may include, for example, a $C_{5-10}$cycloalkene-dicarboxylic acid such as cyclohexenedicarboxylic acid.

The bridged ring cycloalkenedicarboxylic acid may include, for example, a bi- or tri-cycloalkenedicarboxylic acid such as norbornenedicarboxylic acid.

The alicyclic aminocarboxylic acid component may include, for example, an aminocycloalkanecarboxylic acid, specifically an amino$C_{5-10}$cycloalkane-carboxylic acid such as aminocyclohexanecarboxylic acid.

The aromatic monomer component has an aromatic ring skeleton. As examples of the aromatic monomer component, there may be mentioned an aromatic (or araliphatic) diamine component, an aromatic (or araliphatic) dicarboxylic acid component, and an aromatic (or araliphatic) aminocarboxylic acid component.

Examples of the aromatic (or araliphatic) diamine component may include a diaminoarene and a bis(aminoalkyl) arene. The diaminoarene may include, for example, a diamino$C_{6-14}$arene such as m-phenylenediamine, p-phenylenediamine, and m-xylylenediamine. The bis(aminoalkyl)arene may include, for example, a bis(amino$C_{1-4}$alkyl) arene such as m-xylylenediamine.

Examples of the aromatic (or araliphatic) dicarboxylic acid component may include a benzene dicarboxylic acid, an alkylbenzene dicarboxylic acid, a polycyclic arene dicarboxylic acid, a diarylalkane dicarboxylic acid, a diarylketone dicarboxylic acid, a diarylether dicarboxylic acid, a diarylsulfide dicarboxylic acid, and a diarylsulfone dicarboxylic acid.

The benzene dicarboxylic acid may include, for example, phthalic acid, isophthalic acid, and terephthalic acid. The alkylbenzene dicarboxylic acid may include, for example, a $C_{1-4}$alkyl-benzene dicarboxylic acid such as 4-methylisophthalic acid and 5-methylisophthalic acid.

The polycyclic arene dicarboxylic acid may include, for example, a condensed polycyclic arene dicarboxylic acid and a ring-assemblies (or ring-aggregated) arene dicarboxylic acid.

Examples of the condensed polycyclic arene dicarboxylic acid may include a condensed polycyclic $C_{10-24}$arene-dicarboxylic acid such as a naphthalenedicarboxylic acid, e.g., 1,2-naphthalenedicarboxylic acid, 1,4-naphthalenedicarboxylic acid, 1,5-naphthalenedicarboxylic acid, 1,8-naphthalenedicarboxylic acid, 2,3-naphthalenedicarboxylic acid, 2,6-naphthalenedicarboxylic acid, and 2,7-naphthalenedicarboxylic acid; an anthracenedicarboxylic acid; and a phenanthrenedicarboxylic acid; and preferably a condensed polycyclic $C_{10-14}$arene-dicarboxylic acid.

Examples of the ring-assemblies arene dicarboxylic acid may include a bi$C_{6-10}$arene-dicarboxylic acid such as 2,2'-biphenyldicarboxylic acid, 3,3'-biphenyldicarboxylic acid, and 4,4'-biphenyldicarboxylic acid.

Examples of the diarylalkane dicarboxylic acid may include a di$C_{6-10}$aryl$C_{1-6}$alkane-dicarboxylic acid such as 4,4'-diphenylmethane dicarboxylic acid.

Examples of the diarylketone dicarboxylic acid may include a di($C_{6-10}$aryl)ketone-dicarboxylic acid such as 4,4'-diphenylketone dicarboxylic acid.

Examples of the diarylether dicarboxylic acid may include a di($C_{6-10}$aryl)ether-dicarboxylic acid such as 4,4'-diphenylether dicarboxylic acid.

Examples of the diarylsulfide dicarboxylic acid may include a di($C_{6-10}$aryl)sulfide-dicarboxylic acid such as 4,4'-diphenylsulfide dicarboxylic acid.

Examples of the diarylsulfone dicarboxylic acid may include a di($C_{6-10}$aryl)sulfone-dicarboxylic acid such as 4,4'-diphenylsulfone dicarboxylic acid.

The aromatic aminocarboxylic acid component may include, for example, an aminoarene carboxylic acid. The aminoarene carboxylic acid may include, for example, an amino$C_{6-12}$arene carboxylic acid such as aminobenzoic acid.

These monomer components may be used alone or in combination of two or more for producing the polyamide-series resin. For example, the polyamide-series resin may be formed or produced by polymerizing the diamine component and the dicarboxylic acid component; the aminocarboxylic acid component and/or the lactam component; and the diamine component and the dicarboxylic acid component, and the aminocarboxylic acid component and/or the lactam component. The polyamide-series resin may be a homopolyamide formed with a single monomer component (set of a single diamine component and a single dicarboxylic acid component, a single aminocarboxylic acid component, or a single lactam component); and a copolyamide obtained or produced by copolymerizing a plurality of monomer components. Representative examples of the polyamide-series resin may include an aliphatic polyamide resin, an alicyclic polyamide resin, and an aromatic polyamide resin.

The aliphatic polyamide resin comprises an aliphatic monomer unit derived from the aliphatic monomer component, and may include, for example, a homopolyamide of the aliphatic diamine component and the aliphatic dicarboxylic acid component, such as polyamide 46, polyamide 66, polyamide 610, and polyamide 612; a homopolyamide of the aliphatic aminocarboxylic acid component and/or the lactam component corresponding to the aliphatic aminocarboxylic acid component, such as polyamide 6, polyamide 11, and polyamide 12; a copolymer (copolyamide) of a plurality of aliphatic monomer components, such as copolyamide 6/66, copolyamide 6/11, and copolyamide 66/12.

The alicyclic polyamide resin has an alicyclic monomer unit derived from the alicyclic monomer component, and may be formed with a combination of the aliphatic monomer component and the alicyclic monomer component. Representative examples of the alicyclic polyamide resin may include a homopolyamide of the alicyclic diamine component and the aliphatic dicarboxylic acid component, such as a polymer of diaminomethylcyclohexane and adipic acid.

The aromatic polyamide resin has an aromatic monomer unit derived from the aromatic monomer component, and may include, for example, a semiaromatic polyamide resin formed with the aromatic monomer component, and the aliphatic or alicyclic monomer component; a wholly aromatic polyamide resin or a fully aromatic polyamide resin, which is formed by the aromatic monomer component without the aliphatic monomer component and the alicyclic monomer component.

The semiaromatic polyamide resin may include, for example, a homopolyamide of the aromatic (or araliphatic) diamine component and the aliphatic dicarboxylic acid component, such as polyamide MXD 6 (a polymer of m-xylylenediamine and adipic acid); a homopolyamide of the aliphatic diamine component and the aromatic dicarboxylic acid component, such as polyamide 6T (a polymer of hexamethylenediamine and terephthalic acid), polyamide 9T (a polymer of nonamethylene diamine and terephthalic acid), polyamide 10T (a polymer of decamethylene diamine and terephthalic acid), polyamide 12T (a polymer of dodecamethylene diamine and terephthalic acid), polyamide M5T (a polymer of 2-methylpentamethylene diamine and terephthalic acid), polyamide M8T (a polymer of 2-methyloctamethylene diamine and terephthalic acid), polyamide 6I (a polymer of hexamethylenediamine and isophthalic acid), and a polymer of trimethylhexamethylene diamine and terephthalic acid; a copolymer formed with at least the aliphatic diamine component and the aromatic dicarboxylic acid component, such as copolyamide 6T/66, copolyamide 6T/M5T, copolyamide 6T/6I, copolyamide 6T/6I/6, and copolyamide 6T/6I/66.

The wholly aromatic polyamide resin may include, for example, a homopolyamide of the aromatic diamine component and the aromatic dicarboxylic acid component, such as a polymer of m-phenylenediamine and isophthalic acid, and a polymer of p-phenylenediamine and terephthalic acid.

In this description and claims, the symbol "/" for the copolyamide means that the copolyamide comprises the former and latter monomers (units) with respect to the symbol "/" as a copolymerization component (copolymerization unit). That is, copolyamide 6/66 means a copolymer containing a unit producing polyamide 6 and a unit producing polyamide 66.

The polyamide resin may be a polyamide with a N-alkoxymethyl group, and a polymerized fatty acid-series polyamide resin formed with a dimer acid which is a dimer of an unsaturated higher fatty acid as a polymerization component. The polyamide resin may be crystalline or amorphous. Further, the polyamide resin may be a transparent polyamide resin (amorphous transparent polyamide resin). From a viewpoint of mechanical characteristics of a molded article or a molded object, the polyamide resin is preferably a crystalline resin.

These polyamide-series resins may be used alone or in combination of two or more. Among these polyamide-series resins, the aliphatic polyamide resin is preferred. In particular, the polyamide-series resin is preferably the aliphatic polyamide resin formed with the aliphatic monomer component with an alkylene group having about 4 to 12 carbon atoms, more preferably 6 to 11 carbon atoms, further preferably 6 to 9 carbon atoms, and the polyamide-series resin is particularly the aliphatic polyamide resin having at least alkylene group with 6 carbon atoms. Representative preferred aliphatic polyamide resin is a homopolyamide of the aliphatic diamine component and the aliphatic dicarboxylic acid component, such as polyamide 46, polyamide 66, polyamide 610, and polyamide 612.

The number average molecular weight Mn of the polyamide-series resin is for example 7000 to 1000000, and a preferred range of Mn is 10000 to 750000, 20000 to 500000, 30000 to 500000, and 50000 to 500000 in a stepwise manner. The molecular weight can be for example measured by a conventional means such as gel permeation chromatography (GPC) and other means, and may be evaluated or measured as a molecular weight in terms of polystyrene.

By adding the fluorene derivative represented by the formula (1) as an additive to these resins for forming or producing a resin composition, the fluidity and/or mechanical properties of the resin composition can be improved. In particular, the resin composition preferably contains the polyamide-series resin in view of more effectively improving the melt fluidity.

In the resin composition, a mass ratio of the compound represented by the formula (1) (the fluorene derivative) relative to the resin may for example be selected from a range of about 0.01/99.99 to 50/50 in terms of the former/the latter, and a preferred range of the mass ratio is, in terms of the former/the latter, 0.1/99.9 to 30/70, 0.5/99.5 to 20/80, 1/99 to 15/85, 1/99 to 10/90, 2/98 to 8/92, 3/97 to 7/93, and 4/96 to 6/94 in a stepwise manner. An excessively higher ratio of the fluorene derivative represented by the formula (1) may provide a possibility to significantly reduce or decrease mechanical characteristics of the resin composition; and an excessively lower ratio of the fluorene derivative represented by the formula (1) may provide a possibility not to improve the fluidity, particularly the melt fluidity, and the mechanical characteristics of the resin composition. However, according to the present disclosure, even if the ratio of the fluorene derivative represented by the formula (1) is relatively low, characteristics of the resin can be effectively improved. In particular, when the resin composition contains the polyamide-series resin, the melt fluidity can be further effectively improved without significantly reducing, or while improving the mechanical characteristics.

The resin composition, if necessary, may contain various additives such as a filler or a reinforcing agent, a colorant e.g., a dyestuff and pigment, a conductive agent, a flame retardant, a plasticizer, a lubricant, a stabilizer, a mold releasing agent, an antistatic agent, a dispersing agent, a flowability modifier, a leveling agent, an antifoamer or an antifoaming agent, a surface modifier, a low stress agent, a carbon material, a curing agent or a hardener, and a curing accelerator. The stabilizer may include, for example, an antioxidant, an ultraviolet absorbing agent, and a heat stabilizer. These additives may be used alone or in combination of two or more.

The resin composition can be prepared by mixing the fluorene derivative (the fluidity improving agent or the fluidity improver) and the resin and, if necessary, the other component such as the additive in a conventional manner such as dry blending and melt kneading or melt mixing. The resin composition may be in the form of a pellet and other forms.

When the resin alone, which is free from the fluorene derivative represented by the formula (1), is simply referred to as blank, and the flexural strength of the blank is defined as 100, the flexural strength of the resin composition may for example be about 90 to 150; and a preferred range of the flexural strength is 95 to 130, 100 to 125, and 110 to 120 in a stepwise manner. In particular, the flexural strength of the resin composition containing the polyamide-series resin may for example be about 90 to 110, and is preferably 95 to 105 relative to 100 of the flexural strength of the blank. The flexural strength of the blank may for example be about 1 to 300 MPa; the blank of the resin containing the polyethylene-series resin shows, for example, a flexural strength of 1 to 10 MPa, and preferably 3 to 7 MPa; the blank of the resin containing the polypropylene-series resin has, for example, a flexural strength of 10 to 100 MPa, and preferably 40 to 50 MPa; and the blank of the resin containing the polyamide-series resin has, for example, a flexural strength of 50 to 200 MPa, and preferably 80 to 180 MPa, 100 to 150 MPa, and 110 to 130 MPa in a stepwise manner.

A deflection (flexure) of the resin composition may for example be about 80 to 120, and is preferably 85 to 115, when the deflection of the blank is defined as 100. In particular, the deflection of the resin composition containing the polyamide-series resin may for example be about 90 to 110, and is preferably 95 to 105 relative to 100 of the deflection of the blank. The deflection of the blank is for example 3 to 30 mm, and preferably 5 to 20 mm; the blank of the resin containing the polyethylene-series resin has, for example, a deflection of 10 to 20 mm, and preferably 14 to 18 mm; the blank of the resin containing the polypropylene-series resin shows, for example, a deflection of 8 to 18 mm, and preferably 10 to 15 mm; and the blank of the resin containing the polyamide-series resin has, for example, a deflection of 5 to 15 mm, and preferably 8 to 13 mm.

The flexural modulus of the resin composition may for example be about 90 to 150, and is preferably 100 to 140, and more preferably 110 to 135, when the flexural modulus of the blank is defined as 100. In particular, the flexural modulus of the resin composition containing the polyamide-series resin may for example be about 95 to 115, and is preferably 100 to 110 relative to 100 of the flexural modulus of the blank. The flexural modulus of the blank is for example about 50 to 5000 MPa; the blank of the resin containing the polyethylene-series resin has, for example, a flexural modulus of 50 to 200 MPa, and preferably 70 to 100 MPa; the blank of the resin containing the polypropylene-series resin shows, for example, a flexural modulus of 1000 to 2000 MPa, and preferably 1300 to 1700 MPa; and the blank of the resin containing the polyamide-series resin has, for example, a flexural modulus of 1000 to 5000 MPa, and preferably 2000 to 4000 MPa, 2500 to 3500 MPa, 2700 to 3200 MPa, and 2800 to 3000 MPa in a stepwise manner.

The tensile strength (maximum tensile strength) of the resin composition may for example be about 80 to 130, and is preferably 90 to 120, and more preferably 95 to 110, when the tensile strength of the blank is defined as 100. In particular, the tensile strength of the resin composition containing the polyamide-series resin may for example be about 90 to 115, and is preferably 95 to 110 relative to 100 of the tensile strength of the blank. The tensile strength (maximum tensile strength) of the blank may for example be about 1 to 200 MPa; the blank of the the blank of the polyethylene-series resin shows, for example, the tensile strength of 5 to 50 MPa, and preferably 10 to 20 MPa; the blank of the resin containing the polypropylene-series resin has, for example, a tensile strength of 10 to 100 MPa, and preferably 30 to 40 MPa; and the blank of the resin containing the polyamide-series resin has, for example, a tensile strength of 50 to 150 MPa, and preferably 60 to 120 MPa, 70 to 100 MPa, and 80 to 90 MPa in a stepwise manner.

The tensile strain at strength (the tensile strain at maximum strength) or the nominal tensile strain at strength (the nominal tensile strain at maximum strength) (hereinafter, simply be referred to as strain), of the resin composition may for example be about 70 to 150, and is preferably 80 to 130, and more preferably 90 to 120, when the strain of the blank is defined as 100. In particular, the resin composition containing the polyethylene-series resin unexpectedly increases the strain (or elongation) while maintaining or improving the tensile strength and the tensile modulus. Therefore, the strain of the resin composition containing the polyethylene-series resin may for example be about 100 to 150, and is preferably 105 to 130, and more preferably 110 to 120 relative to 100 of the strain of the blank. The strain of the resin composition containing the polyamide-series resin may for example be about 85 to 105, and is preferably 90 to 100 relative to 100 of the strain of the blank. The strain of the blank may for example be about 0.1 to 1000%; the blank of the resin containing the polyethylene-series resin has, for example, a nominal tensile strain at (maximum) strength of 100 to 1000%, preferably 300 to 700%, and more preferably 400 to 600%; the blank of the resin containing the polypropylene-series resin shows, for example, a tensile strain at (maximum) strength of 1 to 20%, and preferably 5 to 12%; and the blank of the resin containing the polyamide-series resin has, for example, a tensile strain at (maximum) strength of 1 to 10%, and preferably 2 to 8%, 3 to 7%, 3.5 to 6%, and 4 to 51 in a stepwise manner.

The tensile modulus of the resin composition may for example be about 90 to 150, and is preferably 100 to 140, and more preferably 110 to 135 when the tensile modulus of the blank is defined as 100. The tensile modulus of the resin composition containing the polyamide-series resin may for example be about 95 to 115, and is preferably 100 to 110 relative to 100 of the tensile modulus of the blank. The tensile modulus of the blank may for example be about 50 to 5000 MPa; the blank of the resin containing the polyethylene-series resin has, for example, a tensile modulus of 50 to 200 MPa, and preferably 70 to 100 MPa; the blank of the resin containing the polyethylene-series resin has, for example, a tensile modulus of 1000 to 2500 MPa, and preferably 1500 to 2000 MPa; and the blank of the resin containing the polyamide-series resin has, for example, a tensile modulus of 1000 to 5000 MPa, and preferably 2000 to 4000 MPa, 2500 to 3500 MPa, 2800 to 3200 MPa, and 2900 to 3100 MPa in a stepwise manner.

Izod impact strength of the resin composition may for example be about 70 to 120, and is preferably 80 to 110, and more preferably 90 to 100 when Izod impact strength of the blank is defined as 100. In particular, Izod impact strength of the resin composition containing the polyamide-series resin may for example be about 70 to 90, and is preferably 75 to 85 relative to 100 of Izod impact strength of the blank. Izod impact strength of the blank may for example be about 1 to 10 kJ/m$^2$; the blank of the resin containing the polypropylene-series resin has, for example, Izod impact strength of 1 to 5 kJ/m$^2$, and preferably 2 to 4 kJ/m$^2$; the blank of the resin containing the polyamide-series resin has, for example, Izod impact strength of 4 to 7 kJ/m$^2$, and preferably 4.5 to 6.5 kJ/m$^2$, and 5 to 6 kJ/m$^2$ in a stepwise manner.

The melt flow rate (MFR) of the resin composition may for example be about 110 to 300, and is preferably 120 to 200, and more preferably 130 to 180 relative to 100 of the MFR of the blank. In particular, the MFR of the resin composition containing the polyamide-series resin may be about 140 to 200, and is preferably 150 to 190, and more preferably 160 to 180 relative to 100 of the MFR of the blank. The MFR of the blank is for example 10 to 100 g/min, and preferably 20 to 60 g/min, 25 to 50 g/min, and 30 to 40 g/min in a stepwise manner.

In this description and claims, the flexural strength, the deflection, the flexural modulus, the tensile strength (maximum tensile strength), the (nominal) tensile strain at strength, the tensile modulus, Izod impact strength, and the MFR can be measured according to the methods described in Examples mentioned below.

The resin composition has excellent fluidity or mechanical characteristics, and therefore, can produce or form a molded article having excellent mechanical characteristics with a high moldability (or productivity). The shape of the molded article is not particularly limited to a specific shape, can be selected depending on the applications, and may for example be a one-dimensional structure such as linear (a line shape) and a thread shape; a two-dimensional structure such as a film shape, a sheet shape, and a plate shape; a threedimensional structure such as a block shape, a rod shape, and a hollow shape, e.g., a pipe shape or a tubular shape.

The molded article can be produced by conventional molding methods such as an injection molding, an injection compression molding, an extrusion molding, a transfer molding, a blow molding, a pressure molding, and a casting molding.

EXAMPLES

The following examples are intended to describe this disclosure in further detail and should by no means be interpreted as defining the scope of the disclosure. The details of the evaluation methods and reagents used are shown below.
[Evaluation Method]
(HPLC)
The HPLC (high performance or high speed liquid chromatograph) measurement was carried out using HPLC instrument manufactured by SHIMADZU CORPORATION, "LCMS-2020", and a column manufactured by SHIMADZU CORPORATION, "KINTEX XB-C18", and acetonitrile/water as a mobile phase. The volume ratio of acetonitrile/water was varied from 50/50 to 95/5 over 10 minutes, and then held at 95/5 for 5 minutes.
($^1$H-NMR)
The sample was dissolved in a heavy solvent (CDCl$_3$) containing tetramethylsilane as an internal standard substance, and the $^1$H-NMR spectrum was measured using a nuclear magnetic resonance instrument (manufactured by Bruker Corporation, "AVANCE III HD").
(Melting Point)
The melting point was measured using an instrument (manufactured by BUCHI, "Melting point M-565") under the condition of a heating rate or programming rate of 0.5° C./min from a temperature of 50° C.
(5% Mass Reduction Temperature)
The temperature, at which the mass of the sample is reduced by 5% by mass, was measured using a Thermogravimeter-Differential Thermal Analyzer (TG-DTA) (manufactured by PerkinElmer, Inc., "TGA-4000") in a nitrogen atmosphere, under the condition of a measurement temperature range of 50 to 400° C. with a heating rate of 10° C./min.
(Solvent Solubility Test)
For each sample and solvent, a sample and a solvent shown in Table 1 below were mixed in a concentration of 3% by mass, and a mixture was shaken by hand for about 10 minutes, and then allowed to stand overnight at a room temperature (temperature of 15 to 25° C.). After that, the solubility of the sample was visually observed and evaluated according to the following criteria.
A: Soluble
B: Soluble, but undissolved residue was visually confirmed
C: Insoluble
(Flexural Test)
The flexural strength, the deflection (flexure), and the flexural modulus were measured in accordance with JIS K 7171. The flexural modulus was calculated or measured by tangent method.
(Tensile Test)
The tensile strength (maximum tensile strength), the tensile strain at strength (or the nominal tensile strain at strength), and the tensile modulus were measured in accordance with JIS K 7161-1, and -2 under the condition of a test speed of 5 mm/min. The tensile modulus was calculated or measured by tangent method.

(Izod Impact Test (Notched Specimens)
Izod impact strength was measured in accordance with JIS K7110.
(MFR)
The MFR was measured in accordance with JIS K 7210-1, B method under the conditions of the retention time of 5 minutes, the temperature of 280° C., and test load of 1.2 kg.
[Reagents and Others]
(Raw Material)
N,N-diethylacrylamide: "DEAA (registered trademark)", manufactured by KJ Chemicals Corporation
N,N-dimethylacrylamide: "DMAA (registered trademark)", manufactured by KJ Chemicals Corporation
N-isopropylacrylamide: "NIPAM (registered trademark)", manufactured by KJ Chemicals Corporation
N-acryloylmorpholine: "ACMO (registered trademark)", manufactured by KJ Chemicals Corporation
Acrylamide: manufactured by FUJIFILM Wako Pure Chemical Corporation Others DMSO: dimethyl sulfoxide, manufactured by KANTO CHEMICAL CO., INC.
Toluene: manufactured by KANTO CHEMICAL CO., INC.
TBAB: tetrabutylammonium bromide, manufactured by Tokyo Chemical Industry Co., Ltd.
KOH: potassium hydroxide, manufactured by KANTO CHEMICAL CO., INC.
Isopropanol: manufactured by KANTO CHEMICAL CO., INC.

Example 1

After charging 19.4 g (0.117 mol) of 9H-fluorene, 30 mL of DMSO, 30 mL of toluene, 0.6 g (0.0019 mol) of TBAB, and 30.5 g (0.24 mol) of N,N-diethylacrylamide into a reactor equipped with a magnetic stirrer and a three-way cock, and replacing the inner atmosphere of the reactor with nitrogen, the temperature was raised to 65° C. to confirm that the solid matters were completely dissolved. To the resultant solution, 0.56 g of 48% by mass KOH aqueous solution (0.0048 mol (4.8 mmol) in terms of KOH) was added, then the temperature was raised to 90° C., and the mixture was stirred while heating for 2 hours. When the disappearance of 9H-fluorene was confirmed by HPLC, the reaction was terminated. The obtained reaction mixture was cooled to 50° C., and was subjected to a neutralization treatment by adding 0.9 g of 10% by mass HCl aqueous solution (0.0025 mol (2.5 mmol) in terms of HCl) and 17 mL of ion-exchanged water to the reaction solution with stirring. Then, the neutralized mixture was subjected to an extraction with toluene (18.1 g), and a saturated saline (36.1 g, 3 times). The separated extract (toluene phase) was allowed to stand overnight while being cooled to 0° C., so that white crystals were precipitated. The crystals were separated by filtration, and the residue was washed with ion-exchanged water (37.3 mL), and isopropanol (10 mL) to obtain 30.2 g of the objective product represented by the following formula (1-1) (DEAA-FL; yield 61.4%).

The obtained DEAA-FL had the melting point of 87 to 89° C., and the 5% mass reduction temperature of 294° C. Further, the result of $^1$H-NMR of the obtained DEAA-FL is shown below and in FIG. 1.

[Chem. 10]

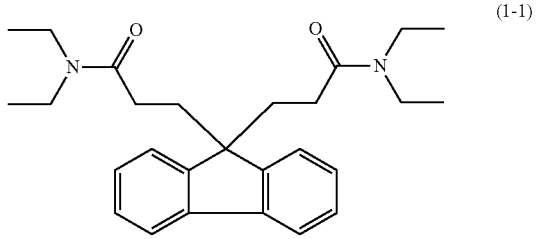

$^1$H-NMR (CDCl$_3$, 300 MHz): δ (ppm)=7.69-7.72 (2H, m), 7.27-7.43 (6H, m), 3.18 (4H, q), 2.79 (4H, q), 2.42-2.48 (4H, m), 1.47-1.53 (4H, m), 0.96 (6H, t), 0.76 (6H, t)

Example 2

After charging 19.4 g (0.117 mol) of 9H-fluorene, 30 mL of DMSO, 30 mL of toluene, 0.6 g (0.0019 mol) of TBAB, and 23.8 g (0.24 mol) of N,N-dimethylacrylamide into a reactor equipped with a magnetic stirrer and a three-way cock, and replacing the inner atmosphere of the reactor with nitrogen, the temperature was raised to 65° C. to confirm that the solid matters were completely dissolved. To the resultant solution, 0.56 g of 48% by mass KOH aqueous solution (0.0048 mol (4.8 mmol) in terms of KOH) was added, then the temperature was raised to 90° C., and the mixture was stirred while heating for 2 hours. When the disappearance of 9H-fluorene was confirmed by HPLC, the reaction was terminated. After cooling the obtained reaction mixture to 50° C., 0.9 g of 10% by mass HCl aqueous solution (0.0025 mol (2.5 mmol) in terms of HCl) and 17 mL of ion-exchanged water were added to the cooled reaction mixture, and the resulting mixture was stirred, so that white crystals gradually precipitated to form white suspension. The suspension was subjected to a filtration, and the residue was washed with hot water (77.7 mL) and isopropanol (15 mL) to obtain 30.0 g of the objective product represented by the following formula (1-2) (DMAA-FL; yield 82.4%).

The obtained DMAA-FL had the melting point of 158 to 159° C., and the 5% mass reduction temperature of 318° C. Further, the result of $^1$H-NMR of the obtained DMAA-FL is shown below and in FIG. 2.

[Chem. 11]

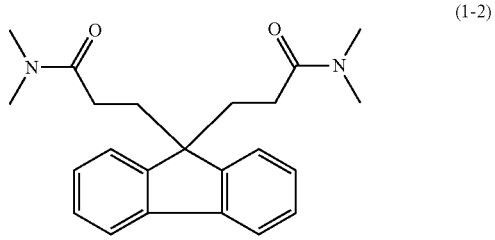

$^1$H-NMR (CDCl$_3$, 300 MHz): δ (ppm)=7.70-7.71 (2H, m), 7.27-7.41 (6H, m), 2.74 (6H, s), 2.51 (6H, s), 2.42-2.47 (4H, m), 1.48-1.54 (4H, m)

Example 3

Example 3A

After charging 19.4 g (0.117 mol) of 9H-fluorene, 30 mL of DMSO, 30 mL of toluene, 0.6 g (0.0019 mol) of TBAB, and 27.2 g (0.24 mol) of N-isopropylacrylamide into a reactor equipped with a magnetic stirrer and a three-way cock, and replacing the inner atmosphere of the reactor with nitrogen, the temperature was raised to 65° C. to confirm that the solid matters were completely dissolved. To the resultant solution, 0.56 g of 48% by mass KOH aqueous solution (0.0048 mol (4.8 mmol) in terms of KOH) was added, then the temperature was raised to 90° C., and the mixture was stirred while heating for 2 hours. When the disappearance of 9H-fluorene was confirmed by HPLC, the reaction was terminated. After cooling the obtained reaction mixture to 50° C., 0.9 g of 10% by mass HCl aqueous solution (0.0025 mol (2.5 mmol) in terms of HCl) and 17 mL of ion-exchanged water were added to the cooled reaction mixture, and the resulting mixture was stirred, so that white crystals gradually precipitated to form a white suspension. The suspension was subjected to a filtration, and the residue was washed with hot water (77.7 mL) and isopropanol (15 mL) to obtain 32.8 g of the objective product represented by the following formula (1-3) (NIPAM-FL; yield 71.4%).

The obtained NIPAM-FL had the melting point of 235 to 237° C., and the 5% mass reduction temperature of 257° C. Further, the result of $^1$H-NMR of the obtained NIPAM-FL is shown below and in FIG. 3.

[Chem. 12]

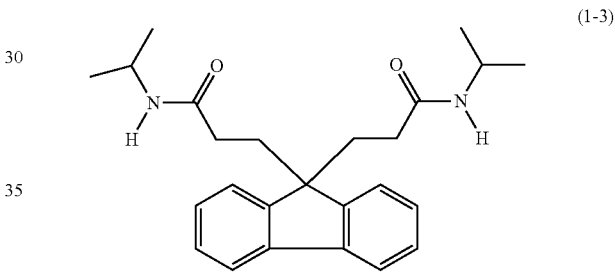

$^1$H-NMR (CDCl$_3$, 300 MHz): δ (ppm)=7.68-7.71 (2H, m), 7.32-7.42 (6H, m), 4.73 (2H, m), 3.84 (2H, m), 2.42 (4H, m), 1.33 (4H, m), 0.97 (12H, d)

Example 3B

NIPAM-FL was synthesized in the same manner as in Example 3A. Methanol was added to the obtained NIPAM-FL to prepare a mixture having a concentration of NIPAM-FL of 10% by mass, the mixture was sealed, and heated to 65° C. to dissolve. The dissolved mixture was stirred for 2 hours while holding at 65° C., and then the resultant mixture was allowed to stand overnight at room temperature (about 20 to 25° C.). The precipitated crystals were collected by suction filtration to obtain NIPAM-FL crystals. The melting point of the obtained NIPAM-FL crystal was the same as that obtained in Example 3A.

Comparative Example 1

After charging 19.4 g (0.117 mol) of 9H-fluorene, 30 mL of DMSO, 30 mL of toluene, 0.6 g (0.0019 mol) of TBAB, and 17.0 g (0.24 mol) of acrylamide into a reactor equipped with a magnetic stirrer and a three-way cock, and replacing the inner atmosphere of the reactor with nitrogen, the temperature was raised to 65° C. to confirm that the solid matters were completely dissolved. To the resultant solution, 0.56 g of 48% by mass KOH aqueous solution (0.0048 mol (4.8 mmol) in terms of KOH) was added, then the temperature was raised to 90° C., and the mixture was stirred while heating for 2 hours. When the disappearance of 9H-fluorene was confirmed by HPLC, the reaction was terminated. After cooling the obtained reaction mixture to 50° C., 0.9 g of 10% by mass HCl aqueous solution (0.0025 mol (2.5 mmol) in terms of HCl) and 17 mL of ion-exchanged water were added to the cooled reaction mixture, and the resulting mixture was stirred, so that white crystals gradually precipitated to form a white suspension. The suspension was subjected to a filtration, and the residue was washed with hot water (77.7 mL) and isopropanol (15 mL) to obtain 31.8 g of the objective product represented by the following formula (AAD-FL; yield 88.4%).

The obtained AAD-FL had the melting point of 254 to 259° C., and the 5% mass reduction temperature of 320° C. Further, the result of $^1$H-NMR of the obtained AAD-FL is shown below and in FIG. 4.

[Chem. 13]

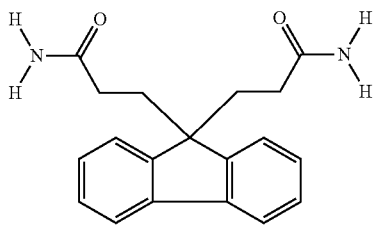

$^1$H-NMR (DMSO-d$_6$, 300 MHz): δ (ppm)=7.82-7.84 (2H, m), 7.47-7.49 (2H, m), 7.35-7.40 (4H, m), 6.97 (2H, s), 6.52 (2H, s), 2.24 (4H, m), 1.26 (4H, m)

Example 4

After charging 19.4 g (0.117 mol) of 9H-fluorene, 30 mL of DMSO, 30 mL of toluene, 0.6 g (0.0019 mol) of TBAB, and 33.8 g (0.24 mol) of N-acryloylmorpholine into a reactor equipped with a magnetic stirrer and a three-way cock, and replacing the inner atmosphere of the reactor with nitrogen, the temperature was raised to 65° C. to confirm that the solid matters were completely dissolved. To the resultant solution, 0.56 g of 48% by mass KOH aqueous solution (0.0048 mol (4.8 mmol) in terms of KOH) was added, then the temperature was raised to 90° C., and the mixture was stirred while heating for 2 hours. When the disappearance of 9H-fluorene was confirmed by HPLC, the reaction was terminated. After cooling the obtained reaction mixture to 50° C., 0.9 g of 10% by mass HCl aqueous solution (0.0025 mol (2.5 mmol) in terms of HCl) and 17 mL of ion-exchanged water were added to the cooled reaction mixture, and the resulting mixture was stirred, so that white crystals gradually precipitated to form a white suspension. The suspension was subjected to a filtration, and the residue was washed with hot water (77.7 mL) and isopropanol (15 mL) to obtain the objective product represented by the following formula (1-4) (ACMO-FL).

[Chem. 14]

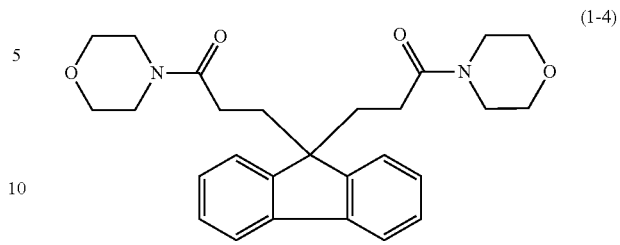

[Evaluation of Solubility]

The results of the solubility test of the fluorene derivatives obtained in Examples 1 to 3 and Comparative Example 1 are shown in Table 1. In Table 1, IPA represents isopropanol, MEK represents methyl ethyl ketone, MIBK represents methyl isobutyl ketone, dioxane represents 1,4-dioxane, and THF represents tetrahydrofuran. As NIPAM-FL, the one prepared in Example 3A was used.

TABLE 1

|  | Example 1 DEAA-FL | Example 2 DMAA-FL | Example 3A NIPAM-FL | Comparative Example 1 AAD-FL |
| --- | --- | --- | --- | --- |
| Water | C | C | C | C |
| Methanol | A | A | A | C |
| Ethanol | A | A | C | C |
| IPA | A | C | C | C |
| Acetone | A | C | C | C |
| MEK | A | C | C | C |
| MIBK | A | A | B | B |
| Ethyl acetate | A | C | C | C |
| Dioxane | A | C | C | C |
| THF | A | A | C | C |
| Toluene | A | C | C | C |
| Hexane | C | C | C | C |
| Chloroform | A | A | C | C |

As apparent from the results in Table 1, the fluorene derivative obtained in Examples had an excellent solubility in solvents as compared with Comparative Example 1.

[Examples 5 to 11, and Comparative Examples 2 to 4] Preparation and Evaluation of Resin Composition For each of Examples and Comparative Examples, a resin composition was prepared by melt-kneading a resin and an additive with the ratio shown in Table 2 (In Comparative Example, without using an additive) using a twin-screw extruder (manufactured by Thermo Fisher Scientific K.K., "Processll Twin Screw Extruder", L/D=40). In examples using PE and PP as the resin, melt-kneading was performed at 260° C., and in examples using PA66 as the resin, melt-kneading was performed at 280° C.

When a thread shaped sample obtained by extruding the resin composition was visually confirmed, the samples in Examples 5, 9 to 11, and Comparative Examples 2 to 4 were not cloudy, and the resin and the additive were compatible with each other.

The flexural test, the tensile test, and Izod impact test of the obtained resin composition were performed, and the MFR thereof was measured. The results are shown in Table 2. Further, the resin for preparing the resin composition is as follows. As NIPAM-FL, the one prepared in Example 3A was used.

PE: polyethylene resin, manufactured by Mitsubishi chemical Corporation, "KERNEL (registered trademark) KC570S"
PP: polypropylene resin, manufactured by Prime Polymer Co., Ltd., "PrimePolypro (registered trademark) J105G"
PA66: polyamide 66, manufactured by Toray industries, Inc. "AMILAN (registered trademark) CM3001"

Regarding the tensile strains in Table 2, the calculated or measured nominal strains are shown in parentheses.

$R^{3a}$ and $R^{3b}$ independently represent a hydrogen atom or a substituent, and $X^{1a}$ and $X^{1b}$ independently represent a group defined in the following formula (X1):

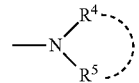

(X1)

TABLE 2

| | Resin | | Additive | | Flexural test | | | Tensile test | | | Izod impact | |
|---|---|---|---|---|---|---|---|---|---|---|---|---|
| | PE | PP | PA66 | DEAA-FL | NIPAM-FL | Flexural strength [MPa] | Deflection [mm] | Modulus [MPa] | Tensile strength [MPa] | (nominal) tensile strain at strength [%] | Modulus [MPa] | strength [KJ/m²] | MFR [g/10 min] |
| | | | | [parts by mass] | | | | | | | | | |
| Comparative Example 2 | 100 | — | — | — | — | 4.29 | 16 | 75.5 | 14.9 | (480) | 73.2 | — | — |
| Example 5 | 95 | — | — | 5 | — | 4.77 | 18 | 73.9 | 15.2 | (570) | 70.1 | — | — |
| Example 6 | 97 | — | — | — | 3 | 4.53 | 15 | 82.8 | 15.3 | (520) | 80.6 | — | — |
| Example 7 | 95 | — | — | — | 5 | 4.67 | 15 | 87.3 | 15.7 | (540) | 81.0 | — | — |
| Example 8 | 90 | — | — | — | 10 | 5.13 | 15 | 101 | 14.8 | (510) | 96.0 | — | — |
| Comparative Example 3 | — | 100 | — | — | — | 46.5 | 13 | 1540 | 35.8 | 7.8 | 1710 | 3.1 | — |
| Example 9 | — | 95 | — | — | 5 | 50.5 | 11 | 1840 | 33.4 | 5.8 | 1960 | 3.0 | — |
| Comparative Example 4 | — | — | 100 | — | — | 118 | 11 | 2920 | 84.5 | 4.4 | 3040 | 5.6 | 35.9 |
| Example 10 | — | — | 95 | 5 | — | 115 | 11 | 2940 | 84.0 | 4.2 | 3160 | 4.4 | 61.9 |
| Example 11 | — | — | 95 | — | 5 | 124 | 11 | 3060 | 88.6 | 4.2 | 3160 | 4.4 | 50.1 |

As apparent from Table 2, each resin composition in Examples improved a mechanical strength such as the flexural strength, the flexural modulus, the tensile strength, and the tensile modulus, and/or the MFR, in comparison with the Comparative Examples.

INDUSTRIAL APPLICABILITY

The fluorene derivative of the present disclosure can be effectively used as an additive (or resin modifier), for example, a strength improving agent and a fluidity improving agent, for improving a mechanical strength and/or a fluidity (melt fluidity or moldability) of a resin.

The invention claimed is:

1. A fluorene derivative represented by the following formula (1):

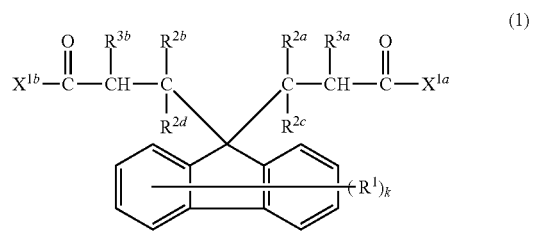

(1)

wherein $R^1$ represents a cyano group, a halogen atom, an alkyl group or an aryl group, k denotes an integer of 0 to 8, $R^{2a}$, $R^{2b}$, $R^{2c}$, and $R^{2d}$ independently represent a hydrogen atom or a substituent, wherein $R^4$ and $R^5$ independently represent a hydrogen atom or an aliphatic hydrocarbon group, provided that the case where both $R^4$ and $R^5$ represent a hydrogen atom is excluded; or $R^4$ and $R^5$ bond together to form a heterocyclic ring containing the nitrogen atom adjacent to $R^4$ and $R^5$.

2. A process for producing the fluorene derivative represented by formula (1) according to claim 1, which comprises allowing a compound represented by the following formula (2):

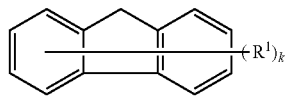

(2)

wherein $R^1$ and k are each defined according to the formula (1) of claim 1, to react with compounds represented by the following formulae (3a) and (3b):

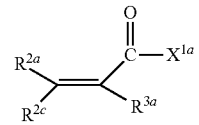

(3a)

-continued

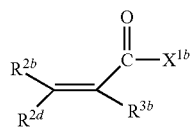

(3b)

wherein $R^{2a}$, $R^{2b}$, $R^{2c}$, and $R^{2d}$, $R^{3a}$ and $R^{3b}$, and $X^{1a}$ and $X^{1b}$ are each defined according to the formula (1) of claim 1.

3. A resin composition comprising the fluorene derivative according to claim 1, and a resin.

4. The resin composition according to claim 3, wherein the resin is at least one resin selected from the group consisting of a polyolefinic resin and a polyamide-series resin.

5. The resin composition according to claim 3, wherein a mass ratio of the fluorene derivative according to claim 1 relative to the resin is 1/99 to 10/90 in terms of the fluorene derivative/the resin.

6. A method for improving fluidity of a resin composition, comprising adding the fluorene derivative according to claim 1 to a resin.

7. A fluidity improving agent that improves fluidity of a resin, the fluidity improving agent comprising the fluorene derivative according to claim 1.

\* \* \* \* \*